US008663672B2

(12) United States Patent
Manrique et al.

(10) Patent No.: US 8,663,672 B2
(45) Date of Patent: *Mar. 4, 2014

(54) OSTEOIMPLANT AND METHOD OF MAKING SAME

(75) Inventors: Albert Manrique, Manalapan, NJ (US); Jean T. Edwards, Hillsboro, NJ (US); Nelson L. Scarborough, Andover, MA (US); Scott D. Boden, Atlanta, GA (US); Kathy Traianedes, North Brunswick, NJ (US); Lawrence A. Shimp, Morganville, NJ (US); James L. Russell, Little Silver, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 814 days.

This patent is subject to a terminal disclaimer.

(21) Appl. No.: 11/231,954

(22) Filed: Sep. 21, 2005

(65) Prior Publication Data

US 2006/0030948 A1 Feb. 9, 2006

Related U.S. Application Data

(60) Division of application No. 10/137,862, filed on May 2, 2002, which is a continuation-in-part of application No. PCT/US01/22853, filed on Jul. 19, 2001.

(60) Provisional application No. 60/219,198, filed on Jul. 19, 2000, provisional application No. 60/288,212, filed on May 2, 2001.

(51) Int. Cl.
*A61K 9/00* (2006.01)
*C12N 5/02* (2006.01)

(52) U.S. Cl.
USPC ............................ 424/422; 424/400; 435/325

(58) Field of Classification Search
USPC .................................. 424/400, 422; 435/325
See application file for complete search history.

(56) References Cited

U.S. PATENT DOCUMENTS

| | | | |
|---|---|---|---|
| 159,334 A | 2/1875 | Kumpf | |
| 781,882 A | 2/1905 | Hunter | |
| 2,516,438 A | 7/1950 | Wheeler | |
| 2,968,593 A | 1/1961 | Rapkin | |
| 3,458,397 A | 7/1969 | Myers et al. | |
| 3,609,867 A | 10/1971 | Hodosh | |
| 3,739,773 A | 6/1973 | Schmitt et al. | |
| 3,790,507 A | 2/1974 | Hodosh | |
| 3,829,904 A | 8/1974 | Ling et al. | |
| 3,891,997 A | 7/1975 | Herbert | |
| 3,922,726 A | 12/1975 | Trentani et al. | |
| 3,947,287 A | 3/1976 | Belde et al. | |
| 4,059,684 A | 11/1977 | Gross et al. | |
| 4,123,806 A | 11/1978 | Amstutz et al. | |
| 4,134,792 A | 1/1979 | Boguslaski et al. | |
| 4,172,128 A | 10/1979 | Thiele et al. | |
| 4,191,747 A | 3/1980 | Scheicher | |
| 4,209,434 A | 6/1980 | Wilson et al. | |
| 4,224,698 A | 9/1980 | Hopson | |
| 4,291,013 A | 9/1981 | Wahlig et al. | |
| 4,294,753 A | 10/1981 | Urist | |
| 4,355,331 A | 10/1982 | Georges et al. | |
| 4,363,319 A | 12/1982 | Altshuler | |
| 4,394,370 A * | 7/1983 | Jefferies | 606/76 |
| 4,430,760 A | 2/1984 | Smestad | |
| 4,440,370 A | 4/1984 | Rood | |
| 4,440,750 A | 4/1984 | Glowacki et al. | |
| 4,450,592 A | 5/1984 | Niederer et al. | |
| 4,458,733 A | 7/1984 | Lyons | |
| 4,472,840 A | 9/1984 | Jefferies | |
| 4,485,097 A | 11/1984 | Bell | |
| 4,512,038 A | 4/1985 | Alexander et al. | |
| 4,516,276 A | 5/1985 | Mittelmeier et al. | |
| 4,563,350 A | 1/1986 | Nathan et al. | |
| 4,563,489 A | 1/1986 | Urist | |
| 4,581,030 A | 4/1986 | Bruns et al. | |
| 4,595,713 A | 6/1986 | St. John | |
| 4,620,327 A | 11/1986 | Caplan et al. | |
| 4,623,553 A | 11/1986 | Ries et al. | |
| 4,627,853 A | 12/1986 | Campbell et al. | |
| 4,636,526 A | 1/1987 | Dorman et al. | |
| 4,637,931 A | 1/1987 | Schmitz | |
| 4,678,470 A | 7/1987 | Nashef et al. | |
| 4,698,375 A | 10/1987 | Dorman et al. | |
| 4,709,703 A | 12/1987 | Lazarow et al. | |
| 4,743,259 A | 5/1988 | Bolander et al. | |
| 4,795,463 A | 1/1989 | Gerow | |

(Continued)

FOREIGN PATENT DOCUMENTS

DE  179 833  2/1905
DE  44 34 459  4/1996

(Continued)

OTHER PUBLICATIONS

U.S. Appl. No. 10/137,862.*

(Continued)

*Primary Examiner* — Ruth Davis
(74) *Attorney, Agent, or Firm* — Sorell Lenna & Schmidt LLP (57) ABSTRACT

An osteoimplant is provided which comprises a coherent aggregate of elongate bone particles, the osteoimplant possessing predetermined dimensions and shape. The osteoimplant is highly absorbent and sponge-like in nature. Also provided herein are a method of fabricating the osteoimplant and a method of repairing and/or treating bone defects utilizing the osteoimplant.

32 Claims, 4 Drawing Sheets

(56) References Cited

U.S. PATENT DOCUMENTS

| | | | |
|---|---|---|---|
| 4,795,467 | A | 1/1989 | Piez et al. |
| 4,824,939 | A | 4/1989 | Simpson |
| 4,842,604 | A | 6/1989 | Dorman et al. |
| 4,857,269 | A | 8/1989 | Wang et al. |
| 4,863,472 | A | 9/1989 | Tormala et al. |
| 4,888,366 | A | 12/1989 | Chu et al. |
| 4,902,296 | A | 2/1990 | Bolander et al. |
| 4,919,939 | A | 4/1990 | Baker |
| 4,932,973 | A | 6/1990 | Gendler |
| 4,946,792 | A | 8/1990 | O'Leary |
| 4,950,296 | A | 8/1990 | McIntyre |
| 4,961,707 | A | 10/1990 | Magnusson et al. |
| 4,975,526 | A | 12/1990 | Kuberasampath et al. |
| 4,994,030 | A | 2/1991 | Glowczewskie, Jr. et al. |
| 5,001,169 | A | 3/1991 | Nathan et al. |
| 5,007,930 | A | 4/1991 | Dorman et al. |
| 5,015,247 | A | 5/1991 | Michelson |
| 5,032,445 | A | 7/1991 | Scantlebury et al. |
| 5,053,049 | A | 10/1991 | Campbell |
| 5,073,373 | A | 12/1991 | O'Leary et al. |
| 5,092,887 | A | 3/1992 | Gendler |
| 5,108,399 | A | 4/1992 | Eitenmuller et al. |
| 5,112,354 | A | 5/1992 | Sires |
| 5,123,925 | A | 6/1992 | Smestad et al. |
| 5,139,527 | A | 8/1992 | Redl et al. |
| 5,162,114 | A | 11/1992 | Kuberasampath et al. |
| 5,171,278 | A | 12/1992 | Pisharodi |
| 5,171,574 | A | 12/1992 | Kuberasampath et al. |
| 5,197,882 | A | 3/1993 | Jernberg |
| 5,207,710 | A | 5/1993 | Chu et al. |
| 5,236,456 | A | 8/1993 | O'Leary et al. |
| 5,284,655 | A | 2/1994 | Bogdansky et al. |
| 5,290,558 | A | 3/1994 | O'Leary et al. |
| 5,298,254 | A | 3/1994 | Prewett et al. |
| 5,306,304 | A | 4/1994 | Gendler |
| 5,314,476 | A | 5/1994 | Prewett et al. |
| 5,314,478 | A | 5/1994 | Oka et al. |
| 5,329,846 | A | 7/1994 | Bonnuti |
| 5,343,877 | A | 9/1994 | Park |
| 5,366,507 | A | 11/1994 | Sottosanti |
| 5,368,859 | A | 11/1994 | Dunn et al. |
| 5,405,390 | A | 4/1995 | O'Leary et al. |
| 5,405,402 | A | 4/1995 | Dye et al. |
| 5,425,639 | A | 6/1995 | Anders |
| 5,425,762 | A | 6/1995 | Muller |
| 5,432,000 | A | 7/1995 | Young et al. |
| 5,439,684 | A | 8/1995 | Prewett et al. |
| 5,441,517 | A | 8/1995 | Kensey et al. |
| 5,447,725 | A | 9/1995 | Damani et al. |
| 5,449,375 | A | 9/1995 | Vidal et al. |
| 5,455,041 | A | 10/1995 | Genco et al. |
| 5,464,439 | A | 11/1995 | Gendler |
| 5,476,880 | A | 12/1995 | Cooke et al. |
| 5,480,436 | A | 1/1996 | Bakker et al. |
| 5,484,601 | A | 1/1996 | O'Leary et al. |
| 5,490,962 | A | 2/1996 | Cima et al. |
| 5,496,375 | A | 3/1996 | Sisk |
| 5,507,813 | A | 4/1996 | Dowd et al. |
| 5,510,396 | A | 4/1996 | Prewett et al. |
| 5,518,680 | A | 5/1996 | Cima et al. |
| 5,531,791 | A | 7/1996 | Wolfinbarger, Jr. |
| 5,545,222 | A | 8/1996 | Bonutti |
| 5,556,430 | A | 9/1996 | Gendler |
| 5,567,806 | A | 10/1996 | Abdul-Malak et al. |
| 5,607,269 | A | 3/1997 | Dowd et al. |
| 5,641,518 | A | 6/1997 | Badylak et al. |
| 5,656,593 | A | 8/1997 | Kuberasampath et al. |
| 5,662,710 | A | 9/1997 | Bonutti |
| 5,676,146 | A * | 10/1997 | Scarborough ............... 600/431 |
| 5,683,459 | A | 11/1997 | Brekke |
| 5,700,479 | A | 12/1997 | Lundgren |
| 5,707,962 | A | 1/1998 | Chen et al. |
| 5,723,117 | A | 3/1998 | Nakai et al. |
| 5,727,945 | A | 3/1998 | Dannenbaum |
| 5,782,919 | A | 7/1998 | Zdeblick et al. |
| 5,807,437 | A | 9/1998 | Sachs et al. |
| 5,846,484 | A | 12/1998 | Scarborough et al. |
| 5,888,219 | A | 3/1999 | Bonutti |
| 5,899,939 | A | 5/1999 | Boyce et al. |
| 5,910,315 | A | 6/1999 | Stevenson et al. |
| 5,922,753 | A | 7/1999 | Petrie et al. |
| 6,030,635 | A | 2/2000 | Gertzman et al. |
| 6,090,998 | A | 7/2000 | Grooms et al. |
| 6,123,731 | A * | 9/2000 | Boyce et al. ............... 623/23.63 |
| 6,132,472 | A | 10/2000 | Bonutti |
| 6,206,923 | B1 | 3/2001 | Boyd et al. |
| 6,224,630 | B1 | 5/2001 | Bao et al. |
| 6,294,187 | B1 | 9/2001 | Boyce et al. |
| 6,311,690 | B1 | 11/2001 | Jefferies |
| 6,326,018 | B1 | 12/2001 | Gertzman et al. |
| 6,340,477 | B1 | 1/2002 | Anderson |
| 6,361,565 | B1 | 3/2002 | Bonutti |
| 6,375,663 | B1 | 4/2002 | Ebner et al. |
| 6,432,436 | B1 | 8/2002 | Gertzman et al. |
| 6,436,138 | B1 | 8/2002 | Dowd et al. |
| 6,436,139 | B1 | 8/2002 | Shapiro et al. |
| 6,437,018 | B1 | 8/2002 | Gertzman et al. |
| 6,458,375 | B1 | 10/2002 | Gertzman et al. |
| 6,599,515 | B1 | 7/2003 | Delmotte |
| 6,599,520 | B2 | 7/2003 | Scarborough et al. |
| 6,616,698 | B2 | 9/2003 | Scarborough |
| 6,630,153 | B2 | 10/2003 | Long et al. |
| 6,632,247 | B2 | 10/2003 | Boyer et al. |
| 6,638,309 | B2 | 10/2003 | Bonutti |
| 6,652,592 | B1 | 11/2003 | Grooms et al. |
| 6,652,593 | B2 | 11/2003 | Boyer, II et al. |
| 6,706,067 | B2 | 3/2004 | Shimp et al. |
| RE38,522 | E | 5/2004 | Gertzman et al. |
| 6,733,534 | B2 | 5/2004 | Sherman |
| 6,736,853 | B2 | 5/2004 | Bonutti |
| 6,776,938 | B2 | 8/2004 | Bonutti |
| 6,808,585 | B2 * | 10/2004 | Boyce et al. ............... 156/244.11 |
| 6,843,807 | B1 | 1/2005 | Boyce et al. |
| 6,855,169 | B2 | 2/2005 | Boyer, II et al. |
| 6,863,694 | B1 | 3/2005 | Boyce et al. |
| 6,911,212 | B2 | 6/2005 | Gertzman et al. |
| 6,913,621 | B2 | 7/2005 | Boyd et al. |
| 7,045,141 | B2 | 5/2006 | Merboth et al. |
| 7,163,691 | B2 | 1/2007 | Knaack et al. |
| RE39,587 | E | 4/2007 | Gertzman et al. |
| 7,311,713 | B2 | 12/2007 | Johnson et al. |
| 7,323,193 | B2 | 1/2008 | Morris et al. |
| 2001/0020186 | A1 | 9/2001 | Boyce |
| 2002/0026244 | A1 | 2/2002 | Trieu |
| 2002/0029084 | A1 | 3/2002 | Paul et al. |
| 2002/0035401 | A1 | 3/2002 | Boyce et al. |
| 2002/0055143 | A1 | 5/2002 | Bell et al. |
| 2002/0107570 | A1 | 8/2002 | Sybert et al. |
| 2002/0120338 | A1 | 8/2002 | Boyer, II et al. |
| 2002/0161449 | A1 | 10/2002 | Muschler |
| 2003/0009235 | A1 | 1/2003 | Manrique et al. |
| 2003/0036800 | A1 | 2/2003 | Meredith |
| 2003/0045934 | A1 | 3/2003 | Bonutti |
| 2003/0093154 | A1 | 5/2003 | Estes et al. |
| 2004/0023387 | A1 | 2/2004 | Morris et al. |
| 2004/0097612 | A1 | 5/2004 | Rosenberg et al. |
| 2004/0220681 | A1 | 11/2004 | Cole et al. |
| 2005/0065214 | A1 | 3/2005 | Kronenthal |
| 2005/0170396 | A1 | 8/2005 | Baker et al. |
| 2006/0002976 | A1 | 1/2006 | Kronenthal |
| 2006/0013857 | A1 | 1/2006 | Kronenthal |
| 2006/0030948 | A1 | 2/2006 | Manrique et al. |
| 2006/0147545 | A1 | 7/2006 | Scarborough et al. |
| 2006/0280801 | A1 | 12/2006 | Kronenthal |

FOREIGN PATENT DOCUMENTS

| | | |
|---|---|---|
| DE | 29608321 | 8/1996 |
| EP | 0 082 621 | 6/1983 |
| EP | 0 243 151 | 10/1987 |
| EP | 0 267 015 | 5/1988 |
| EP | 0 321 442 A3 | 6/1989 |
| EP | 0 366 029 A3 | 5/1990 |
| EP | 0 406 856 | 1/1991 |

(56) References Cited

FOREIGN PATENT DOCUMENTS

| | | |
|---|---|---|
| EP | 0405429 | 1/1991 |
| EP | 0 411 925 | 2/1991 |
| EP | 0 413 492 | 2/1991 |
| EP | 0 419 275 | 3/1991 |
| EP | 0 483 944 | 5/1992 |
| EP | 0 495 284 | 7/1992 |
| EP | 0 520 237 | 12/1992 |
| EP | 0 555 807 | 8/1993 |
| EP | 0 567 391 | 10/1993 |
| EP | 0 693 523 | 1/1996 |
| EP | 1 142 581 A2 | 10/2001 |
| FR | 2691901 | 12/1993 |
| GB | 2175807 | 10/1986 |
| JP | 9059/1986 | 3/1986 |
| JP | 2121652 | 5/1990 |
| JP | 3210270 A | 9/1991 |
| JP | 4097747 A | 2/1992 |
| JP | 9506281 | 6/1997 |
| RU | 0880425 | 11/1981 |
| WO | WO 86/07265 | 12/1986 |
| WO | WO 89/04646 | 6/1989 |
| WO | WO 89/11880 | 12/1989 |
| WO | WO 94/21196 | 9/1994 |
| WO | WO 95/15776 | 6/1995 |
| WO | WO 96/39203 | 12/1996 |
| WO | WO 97/25941 A1 | 7/1997 |
| WO | WO 98/00183 | 1/1998 |
| WO | WO 98/17209 | 4/1998 |
| WO | WO 98/40113 | 9/1998 |
| WO | WO 99/39757 A1 | 8/1999 |
| WO | WO 00/34556 | 6/2000 |
| WO | WO 00/35510 | 6/2000 |
| WO | WO 00/50102 A1 | 8/2000 |
| WO | WO 01/08584 | 8/2001 |
| WO | WO 02/02156 | 1/2002 |
| WO | WO 02/47587 A | 6/2002 |
| WO | WO 2004/108023 A | 12/2004 |
| WO | WO 2006/057011 A2 | 6/2006 |
| WO | WO 2006/076712 A2 | 7/2006 |

OTHER PUBLICATIONS

Abel, E. "The vapor Phase above the System Sulfuric Acid-Water." J. Phys. Chem. 50(3), pp. 260-283. (1946).

Abjornson et al., "A Novel Approach to Bone Grafting Substitutes", Society for Biomaterials, p. 1372 (2000).

Block, Michael S., D.M.D. et al., "Bone Maintenance 5 to 10 years After Sinus Grafting", J. Oral Maxillofacial Surg., vol. 56, pp. 706-714, 1998.

Bobyn et al., "The Optimum Pore Size for the Fixation of Porous-Surfaced Metal Implants by Ingrowth of Bone", Clinical Orthopaedics and Related Research, 1980, pp. 263-270.

Bolander et al.,"The Use of Demineralized Bone Matrix ion te Repair of Segmental Defects", *The Journal of Bone and Joint Surgery*, vol. 68-A, No. 8, pp. 1264-1273.

Bostrom et al., "Use of Bone Morphogeneic Protein-2 in the Rabbit Ulnar Nonunion Model", Clinical Orthopaedics and Related Research, No. 327, pp. 272-282 (1996).

Covey et al., "Clinical Induction of Bone Repair with Demineralized Bone Matrix or a Bone Morphogenetic Protein", Orthopaedic Review, Aug. 1989, vol. XVII, No. 8, pp. 857-863.

Crowe et al., "Inhibition of Enzymatic Digestion of Amylose by Free Fatty Acids in Vitro Contributes to Resistant Starch Formation", J. Nutr. 130(8): 2006-2008, 2000.

Edwards et al., "Osteoinduction of Human Demineralized Bone: Characterization in a Rat Model", *Clinical Orthopaedics & Rel. Res.* 357:219-228, Dec. 1998.

Gekko et al., "Mechanism of Protein Stabilization by Glycerol: Preferential Hydration in Glycerol-Water Mixtures", vol. 20, No. 16, pp. 4667-5676 (1981).

Gepstein et al., "Bridging Large Defects in Bone by Demineralized Bone Matrix in the Form of a Powder", *The Journal of Bone and Joint Surgery*, vol. 69-A, No. 7, pp. 984-991, 1987.

Gher, Marlin E., et al., "Bone Grafting and Guided Bone Regeneration for Immediate Dental Implants in Humans", J. Periodontology, 1994, 65:881-891.

Glowacki et al., "Application of Biological Principle of Induced Osteogenesis for Craniofacial Defects", The Lancet, 1981, vol. 1, No. 8227, pp. 959-962.

Glowacki et al., "Demineralized Bone Implants", *Symposium on Horizons in Plastic Surgery*, vol. 12, No. 2, pp. 233-241, 1985.

Glowacki et al., "Fate of Mineralized and Demineralized Osseous Implants in Cranial Defects", Calcified Tissue Int. 33: 71-76, 1981.

Groeneveld et al., "Mineralized Processes in Demineralized Bone Matrix Grafts in Human Maxillary Sinus Floor Elevations", John Wiley & Sons, Inc. pp. 393-402 (1999).

Habal et al., "Autologous Corticocancellous Bone Paste for Long Bone Discontinuity Defects: An Experimental Approach", Annals of Plastic Surgery, Aug. 1985, vol. 15, No. 23, pp. 138-142.

Ito, Takayasu et al., "Sensitivity of Osteoinductive Activity of Demineralized and Defatted Rat Femur to Temperature and Furation of Heating", Clinical Orthopaedics and Related Research, No. 316, 1995, pp. 267-275.

Jurgensen, K., M.D. et al., "A New Biological Glue for Cartilage-Cartilage-Cartilage Interfaces: Tissue Transglutaminase", Journal of Bone and Joint Surgery, Inc., Feb. 1997, pp. 185-193.

Kaban et al., "Treatment of Jaw Defects with Demineralized Bone Implants", Journal of Oral and Maxillofacial Surgery, pp. 623-626 (Jun. 6, 1998).

Kakiuchi et al., "Human Bone Matrix Gelatin as a Clinical Alloimplant", International Orthopaedics, 9, pp. 181-188 (1985).

Kiviranta et al., "The Rate fo Calcium Extraction During EDTA Decalcification from Thin Bone Slices as Assessed with Atomic Absorption Spectrophometry", Histochemistry 68, 1980, pp. 119-127.

Kubler, et al., "Allogenic bone and Cartilage Morphogenesis", J. Craniomaxillofac. Surg. 19(7): 238-288, 1991.

Lewandrowski et al., "Flexural Rigidity in Partially Demineralized Diaphysical Bone Grafts," *Clin. Ortho. Rel. Res.* 317: 254-262, 1995.

McLaughlin et al., "Enhancements of Bone Ingrowth by the Use of Bone Matrix as a Biologic Cement", Clinical Orthopaedics and Related Research, No. 183, pp. 255-261 (Mar. 1984).

Meijer et al., Radiographic Evaluation of Mandibular Augmentation with Prefabricated Hydroxylapatite/Fibrin Glue Imlants, Journal of Oral and Maxillofacial Surgery, 1997, pp. 138-145.

Mellonig, "Decalicified Freeze-Dried Bone Allograft as an Implant Material in Human Periodontal Defects", *The International Journal of Periodontics and Restorative Dentistry*, pp. 41-45, 1984.

Mellonig, James T. D.D.S., M.S., "Bone Allografts in Periodontal Therapy", Clinical Orthopaedics and Related Research, No. 324, Mar. 1996.

Mulliken, J.B. and Glowacki, "Induced Osteogenesis for Repair and Construction in the Craniofacial Region", J. Plastic and Reconstructive Surgery, May 1980, p. 553-559.

Neigal et al., "Use of Demineralized Bone Implants in Orbital and Craniofacial", Opthal. Plast. Reconstrs. Surg., 12: 108-120, 1996.

Paralkar, et al., PNAS, 100(11): 6736-6740, 2003.

Parma-Benfenati, S., et al., "Histologic Evaluation of New Attachment Utilizing a Titanium-Reinforced Barrier Membrane in a Nucogingival Recession Defect. A Case Report", J. Periodontology, Jul. 1998.

Perez, B.J. et al., "Mechanical properties of a discontinous random fiber composite for totally bioabsorbable fracture fixation devices", Paper presented in : Bioengineering Conference, 1995, Proceedings of the 1995 IEEE 21st Annual Northeast, May 22-23, 1995, pp. 55-56.

Product literature for Bio-Gide®, Resorbable barrier membrane from OsteoHealth Co., Division of Luitpold Pharmaceutical, Inc. 1998.

Product literature for Gore Resolut XT, Bioabsorbable membrane from Gore Regenerative Technologies, Palm Beach Gardens, FL 1998.

Ray, Robert et al. "Bone Implants: Preliminary Report of an Experimental Study", Journal of Bone and Joint Surgery, vol. 29 A (5), Oct. 1957.

Russell et al., *Orthopaedics*, 22(5):524-53, May 1, 1999.

(56) References Cited

OTHER PUBLICATIONS

Stairs, Robert A. "Calculation of Surface Tension of Salt Solutions: effective polarizability of solvated ions." Can. J. Chem. 73: 781-787. 1995.
Stevenson et al., "Factors Affecting Bone Graft Incorporation", Clinical Orthopaedics and Related Research, No. 323, 1996, pp. 66-74.
The Term "Substantially", Merriam-Webster Online Dictionary, at the web—http://www.m-w.com, p. 1.
Teparat, Thitiwan et al., "Clinical Comparison of Bioabsorbable Barriers With Non-Resorbable Barriers in Guided Tissue Regeneration in the Treatment of Human Intrabony Defects", J. Periodontology, Jun. 1998.
Todescan et al., "A Small Animal Model for Investigating Endosseous Dental Impants:Effect of Graft Materials on Healing of Endoss, Porous-Surfaced Implants Placed in a Fresh Extraction Socket", *The Journal of Oral and Maxillofacial Implants*, vol. 2, No. 2, pp. 217-223, 1987.
Ueland et al., "Increased Cortical Bone Content of Insulin-Like Growth Factors in Acromegalic Patients", J. Clin. Endocrinol. Metab., 84(1): 123-127, 1999.
Urist, M.R. et al., "The Bone Induction Principle", *Clin. Orthop. Rel. Res.* 53:243-283, 1967.
Urist, M.R., "Bone Formation by Autoinduction", *Science*, 150(698):893-9,1965.
Whiteman et al., *J. Hand. Surg.* 18B:487, 1993.
Whittaker et al., "Matrix Metalloproteinases and Their Inhibitors—Current Status and Future Challenges", Celltransmissions, 17(1): 3-14.
Xiaobo et al., *Orthop.*, No. 293, pp. 360-365, 1993.
Zhang, et al., "A Quantative Assessment of Osteoinductivity of Human Demineralized Bone Matrix", J. Periodontol. 68(11): 1076-1084, 1997.
Ruppert, Rainer et al. "Human bone morphogenetic protein 2 contains a heparin-binding site which modifies its biological activity," *Eur. J. Biochem*, 237(1): 295-302 (1996).
Kubler, N. R. et al. "EHBMP-2: the first BMP-variant with osteoinductive properties," *Mund Kiefer Gesichtschir*, 3(1): S134-S139 (1999).
Reddi, A. Hari. "Interplay between bone morphogenetic proteins and cognate binding proteins in bone and cartilage development: noggin, chordin and DAN," *Arthritis Research*, 3(1): 1-5 (2001).
Gazzerro, Elisabetta et al. "Bone Morphogenetic Proteins Induce the Expression of Noggin, Which Limits Their Activity in Cultured Rat Osteoblasts," *Jour. of Clin. Invest.*, 102(12): 2106-2114 (1998).

Yamaguchi, Akira. "Recent advances in researches on bone formation—Role of BMP in bone formation," Nihon Rinsyo, 56(6): 1406-1411 (1998).
Dallas, Sarah L. et al. "Dual Role for the Latent Transforming Growth Factor-β Binding Protein in Storage of Latent TGF-β in the Extracellular Matrix and as a Structural Matrix Protein," *Jour. of Cell Biol.*, 131(2): 539-549 (1995).
Pedrozo, Hugo A. et al. "Vitamin D Metabolites Regulate LTBP1 and Latent TGF-β1 Expression and Latent TGF-β1 Incorporation in the Extracellular Matrix of Chohdrocytes," *Jour. of Cell. Biochem.*, 72(1): 151-165 (1999).
Pedrozo, Hugo A. et al. "Growth Plate Chondrocytes Store Latent Transforming Growth Factor (TGF)- β1 in Their Matrix Through Latent TGF-β1 Binding Protein-1," *Jour. of Cellular Physiology*, 177(2): 343-354 (1997).
Bautista, Catalino M. et al. "Isolation of a novel insulin-like growth factor (IGF) binding protein from human bone: A potential candidate for fixing IGF-II in human bone," *Biochem. and Biophys. Research Communications*, 176(2): 756-763 (Apr. 30, 1991).
Mohan, S. "Insulin-Like Growth Factor Binding Proteins in Bone Cell Regulation," Growth Regulation, 3(1): 67-70 (1993).
Japanese Office Action dated Mar. 18, 2009, from related, co-pending application JP2003-533987.
Urist et al. "Bone Formation in Implants of Partially and Wholly Demineralized Bone Matrix," Clinical Orthopaedics and Related Research, vol. 71, pp. 271-278 (1970).
Grafton™ Allogenic Bone Matrix (ABM), Advertising Brochure, Advanced Processing of Human Allograft Bone, Osteotech, Inc., 1992.
Frenkel et al. "Use of Demineralized Bone Matrix Gel to Enhance Spine Fusion", 19th Annual Meeting of the Society for Biomaterials, Apr. 28-May 2, 1993, Birmingham, AL, p. 162.
Stevenson et al. "Long Bone Defect Healing Induced by a New Formulation of Rat Demineralized Bone Matrix Gel," 40th Annual Meeting, Orthopedic Research Society, Feb. 21-24, 1994, New Orleans, LA, p. 205-35.
Lewandrowski et al., "Kinetics of cortical bone demineralization: Controlled demineralization—a new method for modifying cortical bone allografts", J. of Biomedical Materials Research, vol. 31, pp. 365-372 (1996).
Reddi et al., "Biochemical Sequences in the Transformaton of Normal Fibroblasts in Adolescent Rats", *Proc. Nat. Acad. Sci. USA*, vol. 69, pp. 1601-1605 (1972).
JADA, vol. 133, Dec. 2002. http://jada.ada.org/cgi/reprint/133/12/1610-a.

* cited by examiner

OSTEOIMPLANT AND METHOD OF MAKING SAME

CROSS REFERENCE TO RELATED APPLICATIONS

This application is a divisional of U.S. patent application Ser. No. 10,137,862, filed on May 2, 2002, which is a continuation-in-part of International Application No. PCT/US01/22853, filed Jul. 19, 2001, and claims the 35 U.S.C. §119 (e) benefit of provisional applications 60/219,198, filed on Jul. 19, 2000 and 60/288,212 filed May 2, 2001. The entire contents of aforesaid applications 10/137,862, PCT/US01/22853, 60/219,198 and 60/288,212 are incorporated by reference herein.

BACKGROUND OF THE INVENTION

1. Field of the Invention

This invention relates to an osteoimplant of predetermined dimensions and shape made up of a coherent aggregate of elongate bone particles and to a method for making the osteoimplant. Among its other applications, the osteoimplant can be fashioned as a plug for insertion in a space or cavity within an implant used in an orthopedic procedure, e.g., an intervertebral spacer employed in spinal fusion, or for insertion in a cavity associated with a relatively well-defined bone defect, e.g., an extraction socket, a bore hole, etc.

2. Description of the Related Art

Shaped or cut bone elements have been used extensively to treat various medical problems in human and animal orthopedic surgical practice. The use of such bone has also extended to the fields of, e.g., cosmetic and reconstructive surgery, dental reconstructive surgery, podiatry, orthopaedics, neurosurgery and other medical fields involving hard tissue. The use of autograft bone (where the patient provides the source), allograft bone (where another individual of the same species provides the source) or xenograft bone (where another individual of a different species provides the source) is well known in both human and veterinary medicine. In particular, transplanted bone is known to provide support, promote healing, fill bony cavities, separate bony elements (such as vertebral bodies), promote fusion (where bones are induced to grow together into a single, solid unit) or stabilize the sites of fractures. More recently, processed bone has been developed into shapes for use in new surgical applications or as new materials for implants that were historically based on non-biologically derived materials.

A particularly advantageous application of shaped or cut bone elements, particularly those derived from allograft bone, is that involving the fusion of adjacent vertebral bodies where there has been damage or injury to the intervertebral disc.

Intervertebral discs, located between the end plates of adjacent vertebrae, stabilize the spine, distribute forces between vertebrae and cushion vertebral bodies. A normal intervertebral disc includes a semi-gelatinous component, the nucleus pulpous, which is surrounded and confined by an outer fibrous ring, the annulus fibrous. In a healthy, spine, the annulus fibrous prevents the nucleus pulpous from protruding outside the disc space.

Spinal discs may be displaced or damaged due to trauma, disease, or aging. Disruption of the annulus fibrosis allows the nucleus pulposus to protrude into the vertebral canal, a condition commonly referred to as a herniated or ruptured disc. The extruded nucleus pulposus may press upon a spinal nerve, resulting in nerve damage, pain, numbness, muscle weakness and/or paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage in addition to severe pain. Pain relief via discectomy and arthrodesis requires preservation of the disc space and eventual fusion of the affected motion segments.

Bone grafts have been used to fill the intervertebral space to prevent disc space collapse and promote fusion of adjacent vertebrae across the disc space. In early techniques, bone material was simply implanted between adjacent vertebrae, typically at the posterior aspect of the vertebra, and the spinal column was stabilized by way of a plate or rod spanning the affected vertebrae. Once fusion occurred, the hardware used to maintain the stability of the vertebrae became superfluous and became a permanent non-functional foreign body. Moreover, the surgical procedures employed to implant a rod or plate to stabilize the spine while fusion was taking place were frequently lengthy and involved.

It was therefore determined that a better solution to the stabilization of an excised disc space is to fuse the vertebrae between their respective end plates, preferably without the need for anterior or posterior rod or plate. There have been numerous attempts to develop an acceptable intradiscal implant that could be used to replace a damaged disc and maintain the stability of the disc inter space between the adjacent vertebrae, at least until complete arthrodesis is achieved. The implant must provide temporary support and allow bone ingrowth. Success of the discectomy and fusion procedure requires the development of a contiguous growth of bone to create a solid mass because the implant may not withstand the compressive loads on the spine for the life of the patient.

Fusion cages provide a space for inserting a bone graft between adjacent portions of bone. In time, the bone and bone graft grow together through or around the fusion cage to fuse the graft and the bone solidly together. One current use of fusion cages is to treat a variety of spinal disorders, including degenerative disc diseases such as Grade I or II spondylolisthesis of the lumbar spine. Spinal fusion cages (included in the general term, "fusion cages") are inserted into the intervertebral disc space between two vertebrae for fusing them together. They distract (or expand) a collapsed disc space between two vertebrae to stabilize the vertebrae by preventing them from moving relative to each other.

The typical fusion cage is cylindrical, hollow and threaded. Alternatively, some known fusion cages are unthreaded or made in tapered, elliptical, or rectangular shapes. Known fusion cages are constructed from a variety of materials including titanium alloys, porous tantalum, other metals, allograft bone, or ceramic material. For example, U.S. Pat. No. 5,015,247 to Michelson and U.S. Pat. No. 5,782,919 to Zdeblick disclose a threaded spinal cage the contents of which are incorporated herein by reference. The cages are hollow and can be filled with osteogenic material, such as autograft or allograft, prior to insertion into the intervertebral space. Apertures defined in the cage communicate with the hollow interior to provide a path for tissue growth between the vertebral end plates.

Fusion cages may be used to connect any adjacent portions of bone. A primary use is in the lumbar spine. Other sites include the cervical or thoracic segments of the spine. Fusion cages can be inserted in the lumbar spine using an anterior, posterior or lateral approach. Insertion is usually accomplished through a traditional open operation but a laparoscopic or percutaneous insertion technique can also be used.

Spinal fusion cages are typically designed to support vertebrae in the proper geometry during the fusion process and are not intended to provide a long term, permanent support. Actual bone fusion is the ultimate goal. In order to achieve fusion, bone conducting or inducing materials such as bone chips, ceramics, marrow, growth factors, etc., are packed into the cage in order to provide a favorable environment for bony ingrowth. The success of these methods depends to some extent on the surgeon's skill in packing the cages and retaining the materials in the cages during and after implantation. It is especially important that the filler material be in contact with the surfaces of the vertebral bodies on either side of the cage as well as any autograft material(s) employed at the surgical site. While many materials will function as adequate cage filler materials, the best results are obtained with materials that are osteoinductive and not just osteoconductive. Bone grafting materials for use in osteoimplants are described in U.S. Pat. No. 4,950,296, the contents of which are incorporated by reference herein.

Osteoconductive materials are ones that guide bone growth but do not stimulate it. Examples are bone chips and ceramics. Osteoinductive materials actually cause bone to form and result in faster and more certain healing. Examples of osteoinductive materials include cancellous bone, demineralized bone and various growth factors. The most common source of osteoinductive material is the patient's own bone. Typically, in spinal surgery, this is harvested from the iliac crest in the form of bone chips and marrow. While effective, it causes secondary damage (to the harvest site) and requires preparation before it can be used. Furthermore, it is somewhat difficult to maintain in place due to its semi-fluid nature.

Demineralized bone is an alternative to bone chips and marrow as an osteoinductive material. Demineralized bone comes in various forms including powder, gels, pastes, fibers and sheets. The more fluid forms such as powders, gels and pastes are relatively easy to implant at the repair site but difficult to maintain in place. The production of bone powder for filling osteoimplants is disclosed and incorporated herein by reference to U.S. Pat. No. 5,910,315 et al. The process of preparing shaped materials derived from elongate bone particles is incorporated herein by reference to U.S. Pat. No. 5,507,813.

In addition, there is the possibility of wasted material anytime a standard material has to be adapted to fill a cage. Therefore, the need remains for an osteoinductive material that can be used to fill the relatively well-defined cavities of, for example, bone fusion devices, extraction sockets, bore holes, etc. and that doesn't require any special tailoring by the surgeon at the time of implantation yet remains where placed for periods of time sufficient to allow suitable bone fusion to take place. It would be advantageous if methods of producing such a material could be achieved efficiently and accurately by a simple process. The use of such an osteoinductive material at an appropriate surgical site would provide improved outcome for implant recipients.

U.S. Pat. No. 5,507,813 describes a surgically implantable sheet formed from elongate bone particles, optionally those that have been demineralized. The sheet can further contain biocompatible ingredients, adhesives, fillers, plasticizers, etc. The osteoinductive sheet is rigid and relatively strong when dry and flexible and pliable when wetted or hydrated. These sheets are available under the tradename Grafton®Flex (Osteotech, Inc., Eatontown, N.J., USA). The sheets must be wetted/hydrated prior to use in order to render them useful for implantation.

U.S. Pat. No. 4,932,973 describes an artificial organic bone matrix with holes or perforations extending into the organic bone matrix. The holes or perforations are indicated to be centers of cartilage and bone induction following implantation of the bone matrix into living tissue.

U.S. Pat. No. 4,394,370 discloses a one-piece sponge-like bone graft material fabricated from fully demineralized bone powder or microparticulate bone, and reconstituted collagen. The sponge-like graft is optionally crosslinked with glutaraldehyde.

Another one-piece porous implant is described in U.S. Pat. No. 5,683,459. The implant is made up of a biodegradable polymeric macrostructure composed of chemotactic ground substances such as hyaluronic acid.

SUMMARY OF THE INVENTION

It is an object of the invention to provide an osteoimplant of predetermined dimensions and shape derived from elongate bone particles.

It is another object of the invention to provide an osteoimplant fabricated from a coherent aggregate of elongate bone particles wherein the osteoimplant possesses any one of a wide variety of sizes and shapes not limited by the original shape of the bone(s) from which the elongate bone particles are obtained.

It is a particular object of the invention to provide a low density osteoimplant which possesses an open pore structure allowing the osteoimplant to readily absorb fluids such as blood and yet still retain its original shape.

It is another object of the invention to provide an osteoimplant fabricated from elongate bone particles which is flexible when dry and which can be implanted while in the dry state.

It is yet another further object of the invention to provide an method of making an osteoimplant possessing the aforementioned characteristics.

It is still another object of the invention to provide a method of treating a bone defect which utilizes an osteoimplant possessing the aforementioned characteristics.

Another particular object of the invention is the provision of a plug for insertion in a cavity of an implant, e.g., an intervertebral implant, or bone defect site made up of a coherent aggregate of elongate bone particles sized and shaped to substantially fill the cavity of the implant or bone defect site.

These and other objects of the invention are met by the osteoimplant herein which comprises a coherent aggregate of elongate bone particles, the osteoimplant possessing predetermined dimensions and shape.

The term "osteoimplant" as utilized herein is intended to refer to any device or material for implantation that aids or augments bone formation or healing. Osteoimplants are often applied at a bone defect site, e.g., one resulting from injury, defect brought about during the course of surgery, infection, malignancy or developmental malformation. Therefore, such "osteoimplants" are envisioned as being suitably sized and shaped as required for use in a wide variety of orthopedic, neurosurgical, and oral and maxillofacial surgical procedures such as the repair of simple and compound fractures and non-unions, external and internal fixations, joint reconstructions such as arthrodesis, general arthroplasty, deficit filling, discectomy, laminectomy, anterior cervical and thoracic operations, spinal fusions, etc. Therefore, the osteoimplants utilized herein are intended for implantation at a bony site and are made of any biocompatible material(s), e.g., bone or bone particles, biocompatible synthetic materials, combinations thereof, etc, and may be designed for either animal or human use. Specifically, the osteoimplant suitable for use according to the disclosure herein will be any osteoimplant containing at least one defined cavity without limitation to the particular material(s) the osteoimplant is made of or the size or shape of the cavity.

The term "biocompatible" and expressions of like import shall be understood to mean the absence of stimulation of an unacceptable biological response to an implant and is distinguished from a mild, transient inflammation and/or granulation response which can accompany implantation of most foreign objects into a living organism and is also associated with the normal healing response. Materials useful to the invention herein shall be biocompatible if, at the time of implantation, they are present in a sufficiently small concentration such that the above-defined condition is achieved.

The term "particle" as utilized herein is intended to include bone pieces of all shapes, sizes, thickness and configuration such as fibers, threads, narrow strips, thin sheets, clips, shards, powders, etc., that posses regular, irregular or random geometries. It should be understood that some variation in dimension will occur in the production of the particles of this invention and particles demonstrating such variability in dimensions are within the scope in this invention. Particles useful herein can be homogenous, heterogeneous, and can include mixtures of human, xenogenic and/or transgenic material.

The term "human" as utilized herein in reference to suitable sources of implantable materials refers to autograft bone which is taken from at least one site in the graftee and implanted in another site of the graftee as well as allograft bone which is bone taken from a donor other than the graftee.

The term "autograft" as utilized herein refers to tissue that is extracted from the intended recipient of the implant.

The term "allograft" as utilized herein refers to tissue intended for implantation that is, taken from a different member of the same species as the intended recipient.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here in anyway whatsoever.

The expressions "whole bone" and "substantially fully mineralized bone" refer to bone containing its full or substantially full, original mineral content.

The expression "demineralized bone" includes bone that has been partially, fully, segmentally or superficially (surface) demineralized.

The expression "substantially fully demineralized bone" as utilized herein refers to bone containing less than about 8% of its original mineral context.

The term "osteogenic" as applied to the bone plug and/or elongate bone particle composition thereof shall be understood as referring to the ability of an osteoimplant to facilitate or accelerate the growth of new bone tissue by one or more mechanisms such as osteogenesis, osteoconduction and/or osteoinduction.

The term "osteoinduction" shall be understood to refer to the mechanism by which a substance recruits cells from the host that have the potential for forming new bone and repairing bone tissue. Most osteoinductive materials can stimulate the formation of ectopic bone in soft tissue.

The term "osteoconduction" shall be understood to refer to the mechanism by which a non-osteoinductive substance serves as a suitable template or substrate along which bone may grow.

The term "osteogenesis" shall be understood to refer to cell-mediated bone formation.

The term "device" as utilized herein is intended to refer to any osteoimplant that is manufactured predominately of non-bone materials. Such devices are typically made of those materials commonly used in the manufacture of biocompatible implants, e.g., biocompatible metals such as surgical Bioglass®, biocompatible polymeric materials, e.g., polylactic acid, polytetrafluoroethylene, etc., or any other suitable biocompatible non-bone material.

The term "plug" as utilized herein refers to a formed material of predetermined size and shape prepared according to the description herein from a coherent aggregate of elongate bone particles.

The term "cavity" as utilized herein should be understood in the broadest sense possible. Therefore, such term is intended herein to refer to any relatively well-defined space or recess in some other osteoimplant (hereinafter referred to an "implant" to differentiate from the osteoimplant of the invention) or bone defect site. The term cavity is intended to encompass regions contained substantially within the implant, regions defined by an area or portion of the implant, as well as the regions defined by the placement of adjacent implants and regions defined by relatively well-defined bone defects such as extraction sockets, bore holes, etc. Therefore, the term "cavity" as utilized herein broadly includes any relatively well-defined defect at a surgical site.

The plug embodiment of the osteoimplant of the invention is configured to fit within the cavities of commercially available implants, e.g., spinal cages, and relatively well-defined cavities at a surgical site. The plugs are engineered to fit efficiently, are easy to insert and tend to remain where placed. An additional advantage of the plug is that in many of its configurations, it swells somewhat upon contact with body fluids thus ensuring good bone contact at the implant site even where the site is irregularly shaped. The plug, when made from demineralized bone, is generally osteoinductive and the fiber-like shape of the bone particles further provides a favorable scaffold for bone cell growth thus potentially combining osteoconductive and osteoinductive properties.

The plug can be formed in a range of shapes and sizes that fit commercially available osteoimplants, e.g., spinal cages, and relatively well-defined bone defects. Some designs of cages may require two or more shaped plugs. The present invention also provides efficient methods for manufacturing the preformed bone plug and methods of using the preformed bone plug for the surgical treatment and/or repair of a bone defect site.

The term "shaped" as applied to the aggregate of elongate bone particles herein refers to a determined or regular form or configuration in contrast to an indeterminate or vague form or configuration (as in the case of a lump or other solid matrix of no special form) and is characteristic of such materials as sheets, plates, disks, cones, pins, screws, tubes, teeth, bones, portion of bone, wedges, cylinders, threaded cylinders, and the like, as well as more complex geometric configurations.

The term "coherent" as applied to the aggregate of elongate bone particles refers to the ability of the bone particles to adhere to each other either, e.g., by entanglement, or by the use of a biocompatible binder or adhesive.

The expression "three-dimensional" refers to the ability of the coherent aggregate of elongate bone particles to assume any desired shape and size.

The expression "open pore structure" as it applies to the coherent aggregate of elongate bone particles constituting one embodiment of osteoimplant herein shall be understood as referring to the low density, absorbent, sponge-like nature of the osteoimplant in which there are a plurality of accessible pores or openings which are present throughout the entire volume of the aggregate.

The term "incorporation" utilized herein refers to the biological mechanism whereby host tissue gradually replaces the osteoimplant of the invention with native host bone tissue. This phenomenon is also known in the scientific literature as "bone remodeling" or "cellular based remodeling" and "wound healing response". Therefore, the term "incorporation" utilized herein shall be understood as embracing what is conveyed to those skilled in the art by the foregoing expressions.

The expression "further treatment" as utilized herein refers to procedures such as, e.g., lyophilizing, cross-linking treatment, re-mineralization, sterilization, etc., performed either before, during or after the step of making the osteoimplant as well as post-processing procedures such as, e.g., machining, laser etching, welding, assembling of parts, cutting, milling, reactive etching, etc.

Another particularly useful embodiment of the invention herein is an osteoimplant provided as a coherent aggregate, or matrix, of elongate bone particles possessing an open pore structure and a bulk density of less than about 0.3 g/cm$^3$. The open pore structure of the aggregate renders the osteoimplant highly absorbent of surrounding liquids. The osteoimplant formed from the aggregate is flexible when dry (i.e., when containing less than about 5 weight percent water) and does not require time consuming rehydration prior to implantation. It can assume any desired shape and/or configuration and can be cut to the desired dimensions, e.g., with surgical scissors, before and/or after the aggregate has absorbed fluid. Even in the wetted/hydrated state, the osteoimplant will maintain its original shape and coherency and can be readily handled by the medical practitioner.

Osteoinductivity can be conveniently quantified as the amount of bone formed in an ectopic site in an athymic nude rat. Scores are rated 0 to 4. The osteoimplants of the invention exhibit osteoinductivities of at least 2, typically greater than 3, when measured in an athymic rat assay as described in Edwards J T, Diegmann M H, Scarborough N L, Osteoinduction of Human Demineralized Bone: Characterization in an Animal Model, Clin. Orthop. Rel. Res. 357:219 228 (1998).

The osteoimplant of the invention can be combined with a wide variety of biocompatible substances which can be introduced into the porous matrix of the osteoimplant and/or into large cavities, depressions, and the like, produced in the osteoimplant. Thus, the implant herein functions as a highly effective carrier and/or delivery vehicle for bone-growth inducing and/or otherwise medically useful substances.

Further provided herein is a method of fabricating the osteoimplant herein which comprises providing a quantity of elongate demineralized bone particles, mixing the elongate demineralized bone particles with an aqueous wetting agent to provide a fluid composition preferably containing from about 5 to about 40 volume percent swollen, hydrated bone particles, placing the liquid composition in a mold, and removing a sufficient amount of aqueous wetting agent, e.g., by heating the fluid composition in the substantial absence of pressure at elevated temperature, to provide an osteoimplant comprising a shaped, coherent aggregate, or matrix, of elongate bone particles, preferably one of open pore structure and possessing a bulk density of less than about 0.3 g/cm$^3$.

Further provided in accordance with the invention is a method of repairing and/or treating bone comprising implanting at a bone repair site an osteoimplant which comprises a shaped and dimensioned coherent aggregate of elongate bone particles, preferably one of open pore structure and possessing a bulk density of less than about 0.3 g/cm$^3$.

The osteoimplant of the invention can be readily applied to virtually any bone repair site in the body and can be utilized alone or in combination with one or more adjunct medical devices and/or procedures. The osteoimplant of the invention finds particular utility in the areas of dental reconstructive surgery and spinal fusion where substantial amounts of body fluid, e.g., saliva and/or blood, are frequently encountered or where autograft (e.g., local bone, marrow or iliac crest, etc.) is incorporated in the osteoimplant. The unique ability of the osteoimplant to absorb body fluids and still retain its original shape represents a significant advance in the medical field.

DESCRIPTION OF THE PREFERRED EMBODIMENTS

The composition of the osteoimplant herein can be made up of from about 5 to about 100% fully demineralized and/or demineralized elongate bone particles. At least about 50 weight percent, more preferably at least about 60 weight percent, and most preferably at least about 90 weight percent of the bone particles present in the osteoimplant herein are of the elongate variety. Any non-elongate bone particles that are optionally included in the osteoimplant can possess a wide range of dimensions, e.g., powders, chips, etc. The elongate bone particles form a coherent aggregate, or matrix, which imparts porosity and absorbency to the osteoimplant.

The bone component of the osteoimplant can be obtained from cortical, cancellous, and/or corticocancellous allogenic, xenogenic or transgenic bone tissue. In general, allogenic bone tissue is preferred as the source of the bone component. The bone component can be fully mineralized or partially or fully demineralized. Porcine and bovine bones are particularly advantageous types of xenogenic bone tissue that can be used individually or in combination as sources for the bone particles although of course other xenogenic or transgenic bone tissues can also be used. Combinations of fully mineralized and demineralized bone can also be used.

The bone particles employed in the fabrication of the osteoimplant of this invention are generally characterized as "elongate", i.e., they possess relatively high median length to median thickness ratios. In overall appearance, the elongate bone particles can be described as filaments, fibers, threads, slender or narrow strips, etc. Thus, e.g., the elongate bone particles can possess a median length of from about 0.05 to about 200 mm, preferably from about 1 to about 100 mm, a median width of from about 0.05 to about 50 mm, preferably from about 0.1 to about 20 mm, and a ratio of median length to median width of from about 10:1 to about 2000:1, preferably of from about 20:1 to about 600:1. If desired, the elongate bone particles can be graded into different sizes to reduce or eliminate any less desirable size(s) of particles that may be present.

The elongate bone particles can be readily obtained by any one of several methods, e.g., by milling or shaving the surface of an entire bone or relatively large section of bone. Employing a milling technique, one can obtain a mass of elongate bone particles containing at least about 20 weight percent of bone particles coming within the aforesaid range of dimensions.

Another procedure for obtaining the elongate bone particles herein, particularly useful for pieces or sections of bone of up to about 100 mm in length, is the bone processing mill described in commonly assigned U.S. Pat. No. 5,607,269. Use of this bone mill results in the production of long, thin strips which quickly curl lengthwise to provide tubular-like elongate bone particles. The elongate bone particles are optionally subjected to demineralization in accordance with known and conventional procedures in order to reduce their inorganic mineral content. Such demineralization can occur prior to or after forming the elongate particles. Demineralization methods remove the inorganic mineral component of bone by employing acid solutions. Such methods are well known in the art, see for example, Reddi et al., *Proc. Nat. Acad. Sci.* 69, pp 1601-1605 (1972), incorporated herein by reference. The strength of the acid solution, the shape of the bone particles and the duration of the demineralization treatment will determine the extent of demineralization. Reference in this regard may be made to Lewandrowski et al., *J. Biomed Materials Res*, 31, pp. 365-372 (1996), also incorporated herein by reference.

As used herein, the expression "superficially demineralized" refers to bone particles which have undergone surface demineralization as a result of which they possess one or more regions of surface-exposed collagen. The expression "partially demineralized bone" refers to bone possessing less than its original mineral content but not less than about 8 weight percent of its original mineral content. As previously stated, "substantially fully demineralized bone" refers to bone containing less than about 8 weight percent, and usually less than about 3 weight percent, of its original mineral content. Mixtures of one or more of the foregoing types of demineralized bone particles can be employed. Moreover, one or more of the foregoing types of demineralized bone particles can be employed in combination with nondemineralized bone particles, i.e., bone particles that have not been subjected to demineralization. It will be understood by those skilled in the art that fully demineralized bone particles yield a more porous mass compared to whole bone or superficially demineralized bone particles.

When prepared in whole or in part from bone particles that are only superficially demineralized or nondemineralized, the osteoimplant will tend to possess a fairly high compression strength, e.g., one approaching that of natural bone. Accordingly, when an osteoimplant exhibiting rigidity, e.g., a compression strength of on the order of from about 5 to about 200 MPa, preferably from about 20 to about 100 MPa and more preferably from about 25 to about 75 MPa, is desired, superficially demineralized bone particles and/or nondemineralized bone particles are advantageously employed.

In a preferred demineralization procedure, relatively large mineralized bone piece(s) from which demineralized bone particles are subsequently obtained, or fully mineralized bone particles obtained from such relatively large mineralized bone piece(s), are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing microorganisms and viruses. Ordinarily, at least about 10 to 40 percent by weight of water (i.e., about 60 to about 90 weight percent of defatting agent such as alcohol) should be present in the defatting disinfecting solution to produce optimal lipid removal and disinfecting within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water for injection to remove residual amounts of acid and thereby raise the pH. The elongate bone particles used in the manufacture of the plug naturally entangled or may be mechanically entangled employing, e.g., the wet laying procedure, akin to a paper-making process, described in aforementioned U.S. Pat. No. 5,507,813 to Dowd et al., to provide a sheet-like coherent mass of bone particles which can thereafter be shaped, e.g., by cutting, molding, etc., before or after drying and/or other processing into configurations corresponding to those desired for the bone plug of this invention.

If desired, the bone particles before or after their being gathered into a coherent aggregate can be modified in one or more ways, e.g., their protein content can be augmented or modified as described in U.S. Pat. Nos. 4,743,259 and 4,902,296, the contents of which are incorporated by reference herein. The elongate bone particles can also be admixed with one or more substances such as binders/fillers, plasticizers, biostatic/biocidal agents, surface active agents, and the like, prior to, during, or after shaping the elongate bone particles into a desired configuration and size. One or more of such substances can be combined with the bone particles by soaking or immersing the elongate bone particles in a solution or dispersion of the desired substance, by physically admixing the elongate bone particles and the desired substance, co-extrusion of the substance and particles, and the like.

Suitable binders/fillers include cyanoacrylates, epoxy-based compounds, dental resin sealants, dental resin cements, calcium phosphate and calcium sulfate self-setting cements, glass ionomer cements, polymethyl methacrylate, gelatin-resorcinol-formaldehyde glues, protein and collagen-based glues, acrylic resins, cellulosics, bioabsorbable polymers such as polyglycolide, polylactide, glycolide-lactide copolymers, polycaprolactone, polyanhydrides, polycarbonates, polyorthoesters, polyamino acids, polyarylates, polycyanoacrylates, polyhydroxybutyrate, polyhydroxyvalyrate, polyphosphazenes, and polyvinylpyrrolidone, carbohydrate polymers, polyiminocarbonates, polypropylene fumarates, polyanhydride esters, polytetrafluoroethylene, hexacryl, Hyaluronic acid, fibrin, fibrin-collagen, polyethylene glycol glues, mucopolysaccharides, mussel adhesive proteins, fatty acids and fatty acid derivatives, etc.

Other suitable binders/fillers include bone powder, demineralized bone powder, porous calcium phosphate ceramics, hydroxyapatite, tricalcium phosphate, Bioglass® and other calcium phosphate materials, calcium sulfate or calcium carbonate particles, etc.

Suitable plasticizers include liquid poly hydroxy compounds such as glycerol, monoacetin, diacetin, hydrogels, etc.

Suitable biostatic/biocidal agents include antibiotics, povidone, sugars, mucopolysaccharides, etc.

Suitable surface-active agents include the biocompatible nonionic, cationic, anionic and amphoteric surfactants. It will be understood by those skilled in the art that the foregoing list is not intended to be exhaustive and that other materials may be admixed with bone particles within the practice of the disclosure herein such as disclosed in U.S. Pat. No. 5,073,373, the contents of which are incorporated by reference herein.

Any of a variety of bioactive substances can be incorporated in, or associated with, the bone particles before, during or after fabrication of the osteoimplant. Thus, one or more of such substances can be combined with the elongate bone particles by soaking or immersing them in a solution or dispersion of the desired substance(s). Bioactive substances include physiologically or pharmacologically active substances that act locally or systemically in the host.

Representative classes of bioactive factors which can be readily combined with the bone particles include, e.g., trophic factors, analgesics, anti-cancer agents, vaccines, adjuvants, antibodies, neuroleptics, genes and genetic elements for transfection including viral vectors for gene therapy, cells or cellular components, etc. A list of more specific examples would therefore include, collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymicin B, tetracyclines, biomycin, chloromycetin, and streptomycins, cephalosporins, ampicillin, azactam, tobramycin, clindamycin and gentamicin, etc.; biocidal/biostatic sugars such as dextran, glucose, etc.; amino acids, peptides, vitamins, inorganic elements, co-factors for protein synthesis; hormones; endocrine tissue or tissue fragments, synthesizers; enzymes such as collagenase, peptidases, oxidases, etc., polymer cell scaffolds with parenchymal cells, angiogenic drugs and polymeric carriers containing such drugs; collagen lattices; antigenic agents; cytoskeletal agents; cartilage fragments, modified living cells such as chondrocytes, bone marrow cells, mesenchymal stem cells, natural extracts, genetically engineered living cells or otherwise modified living cells, DNA delivered by plasmid or viral vectors, genes or genetic elements, tissue transplants, demineralized bone powder, autogenous tissues such as blood, serum, soft tissue, bone marrow, etc.; bioadhesives; non-collagenous proteins such as osteopontin, osteonectin, bone sialo protein, laminin, fibrinogen, vitronectin, thrombospondin, proteoglycans, decorin, beta glycan, biglycan, aggrecan, versican, tenascin, matrix gla protein, hyaluronan, amino acids, amino acid residues, peptides, bone morphogenic proteins (BMPs); osteoinductive factor (OIF); fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1) (IGF-2); platelet derived growth factors (PDGF); fibroblast growth factors (FGF, aFGF, bFGF, etc.); periodontal ligament chemotactic factor (PDLGF); somatotropin; bone digestors; antitumor agents; immuno-suppressants; fatty acids (including polar and non-polar fatty acids); permeation enhancers, e.g., fatty acid esters such as laureate, myristate and stearate monoesters of polyethylene glycol, enamine derivatives, alpha-keto-aldehydes, etc.; and nucleic acids; inorganic elements, inorganic compounds, cofactors for protein synthesis, hormones, soluble and insoluble components of the immune system; soluble and insoluble receptors including truncated forms; soluble, insoluble and cell surface bound ligands including truncated forms; chemokines, bioactive compounds that are endocytosed; endocrine tissue or tissue fragments, growth factor binding proteins, e.g., insulin-like growth factor binding protein (IGFBP-2) (IGFBP-4) (IGFBP-5) (IGFBP-6); angiogenic agents, bone promoters, cytokines, interleukins, genetic material, genes encoding bone promoting actions, cells containing genes encoding bone promoting action; growth hormones such as somatotrophin; bone digestors; antitumor agents; cellular attractants and attachment agents; immuno suppressants; bone resorption inhibitors and stimulators; angiogenic and mitogenic factors; bioactive factors that inhibit and stimulate secondary messenger molecules; cell adhesion molecules, e.g., cell-matrix and cell-cell adhesion molecules; secondary messengers, monoclonal antibodies specific to cell surface determinants on mesenchymal stem cells, clotting factors; externally expanded autograft or xenograft cells, nucleic acids and any combination thereof. The amounts and types of such optionally added substances can vary widely with optimum levels and combinations being readily determined in a specific case by routine experimentation.

Various shapes of osteoimplant can be made by using extrusion or injection molding techniques, compression molds, pre-formed molds in which the material can be placed to obtain its final shape, or pre-formed shapes which can be used to cut desired shape from pre-formed material. Further to this, devices can be used that allow introduction of various agents in to the molding devices or treatments of the molds to assist in the forming of various shapes, such as, but not limited to, cross linking agents or heat or cooling of the molds and/or during the forming process. Employing such procedures, various sizes and shapes of osteoimplant can be provided such as those illustrated in FIGS. 1a-i.

In one embodiment herein, an osteoimplant as previously described is made by forming demineralized elongate bone particles into a coherent aggregate and thereafter either cutting the osteoimplant from the aggregate or, preferably, to reduce waste, molding the aggregate into an osteoimplant of the desired size and configuration. To fabricate the coherent mass of elongate bone particles, a quantity of elongate bone particles with or without one or more optional materials is mixed with a suitable biocompatible fluid component, e.g., water, organic protein solvent, physiological saline, concentrated saline solution, ionic solution of any kind, aqueous sugar solution, liquid polyhydroxy compound such as glycerol or glycerol ester, hydrogel, etc., or mixtures thereof. The suitable biocompatible fluid can optionally contain one or more substances such as binder, filler, plasticizer, biostatic/biocidal agent, surface active agent, bioactive substance, etc., as previously described to form a slurry or paste. Excess fluid is then removed from the slurry or paste, e.g., by applying the slurry or paste to a mesh or screen and draining away excess fluid. Functionally, the biocompatible fluid provides a coherent aggregate of elongate bone particles whose consistency can be described as shape-sustaining but readily deformable, e.g., putty-like.

If desired, the elongate bone particles can be dried, e.g., at from about 30° to about 80° C. and preferably from about 40° to about 50° C., for from about 1 to about 3 hours, and then lyopbilized under conditions that are well known in the art, e.g., at a shelf temperature of from about −20° to about −35° C., a vacuum of from about 150 to about 100 mTorr and for a period of time ranging from about 4 to about 48 hours. The drying and lyophilization steps will result in the production of a coherent mass of entangled elongate bone particles that is relatively strong when dry and flexible when wetted or hydrated.

In another embodiment of the general method described above, the coherent aggregate of elongate bone particles can be subjected to a compressive force, e.g., of up to about 100,000 psi, during and/or after the step of removing excess liquid and/or while the drained-but-still-wet bone particles are being dried. If desired, the compressed coherent mass can be lyophilized to provide an especially strong and rigid mass.

In yet a further embodiment disclosed herein, the elongate bone particles, in combination with bone particles possessing other geometries such as mineralized and demineralized bone powders and pieces, can be combined with a wetting agent as described above to produce a flowable composition containing from about 5 to about 100%, preferably from about 20 to about 60%, volume percent of bone particles of all types, the remainder of the composition comprising wetting agent. The wetting agent can optionally comprise one or more biocompatible components as previously described. The wetting agent will cause the demineralized elongate bone particles to swell and increase in flexibility. The fluid composition will possess a consistency ranging from a slurry or paste to a wet dough, depending on the amount of wetting agent used. The critical aspect is that the elongate bone particles be suspended in and evenly distributed throughout the fluid composition. This is to be contrasted with the "wet laying" procedure of commonly assigned U.S. Pat. No. 5,507,813 in which wetting agent is substantially removed to produce a dense mat of bone particles.

In this embodiment, the fluid composition is formed by mixing the bone particles and wetting agent to form a liquid slurry, stirring the slurry for a suitable period of time sufficient to allow the wetting agent to penetrate the demineralized elongate bone particles, and removing enough wetting agent, e.g., by draining through a sieve, sufficient to provide a fluid composition containing from about 5 to about 25, preferably from about 10 to about 15, volume percent bone particles. Substantial mechanical entanglement of the elongate bone particles will occur. Suitable wetting agents include biocompatible liquids and/or hydrogels such as previously described. Optionally, the wetting agent can comprise dissolved or admixed therein one or more biocompatible substances such as previously described.

Preferred wetting agents for forming the wetted mass of bone particles include water, liquid polyhydroxy compounds and their esters, and polyhydroxy compounds in combination with water and/or surface active agents. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, polyethylene glycol, polyoxyalkylenes, e.g., Pluronics®, and the like. The preferred polyhydroxy compounds possess up to about 12 carbon atoms and, where their esters are concerned, are preferably the monoesters and diesters. Of these, glycerol is especially preferred as it improves the handling characteristics of the bone particles wetted therewith and is biocompatible and easily metabolized. Most preferred are solutions of polyhydroxy compounds in water, with glycerol/water solutions in weight ratios ranging from about 40:60 to about 5:95, respectively, being especially preferred. Mixtures of polyhydroxy compounds or esters, e.g., sorbitol dissolved in glycerol, glycerol combined with monoacetin and/or diacetin, etc., are also useful.

Where the bone particles have a tendency to quickly or prematurely separate or to otherwise settle out from the fluid composition such that formation of a homogeneous suspension of bone particles in wetting agent is rendered difficult, it can be advantageous to include within the composition a suspension aid. Thus, e.g., where the wetting agent is water and/or glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, xanthan gum, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the wetting agent in an amount sufficient to significantly improve the suspension-keeping characteristics of the composition. Furthermore, suspension aids that generate gas bubbles inside the fluid composition can be employed. The gas bubbles reduce the tendency of the bone particles to settle out and include peroxides and bicarbonate.

Figure 4:
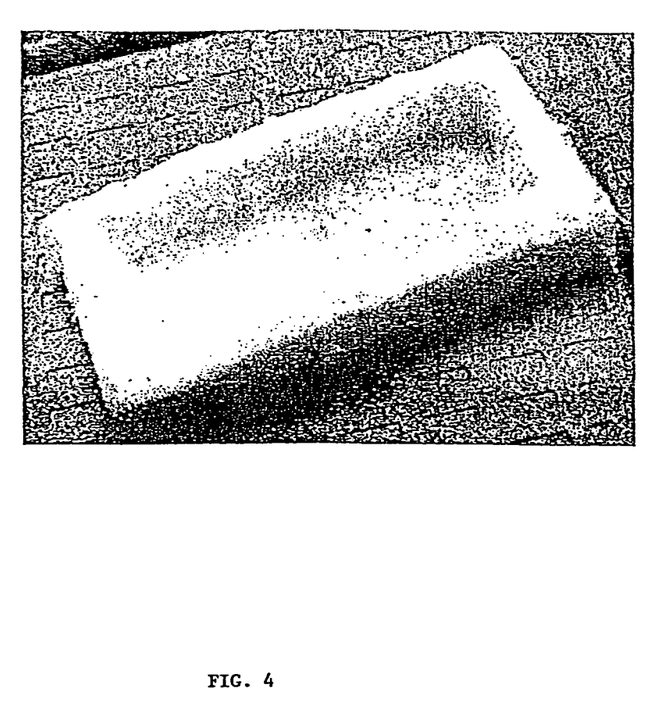
FIG. 4 is a photograph of an osteoimplant produced in accordance with the present invention possessing a preformed cavity or depression; and, FIG. 5 illustrates a mold which can be utilized in the fabrication of an osteoimplant such as that shown in FIG. 4.
Figure 5:
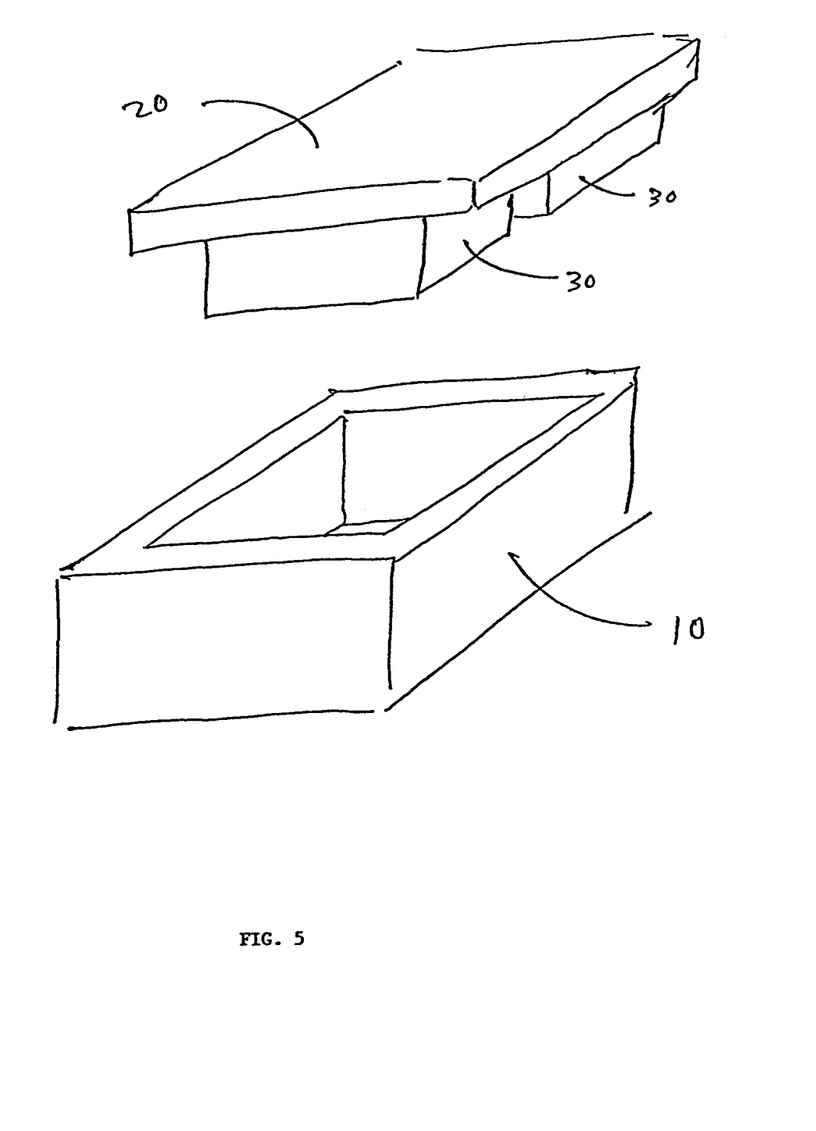

As stated previously, the fluid composition is preferably placed in a mold which optionally is configured and dimensioned in the shape of the final osteoimplant. FIG. 5 depicts mold 10 and lid 20 for mold 10, lid 20 possessing protruding indentations 30. The mold can be optionally configured and dimensioned in the shape of the final osteoimplant, e.g., the osteoimplant shown in FIG. 4. Care must be taken to ensure that minimal, if any, pressure is applied to the composition in the mold which would effect compaction of the elongate bone particles. This is in contrast to the wet-lay procedure described in U.S. Pat. No. 5,507,813. The composition is then dried at a temperature of from about 30° C. to about 80° C., preferably from about 30° C. to about 40° C. to effect removal of water and provide a shaped material. Following the drying step, the shaped material is dried e.g., freeze-dried, employing a shelf temperature of from about −20° to about −35° C. and a vacuum of from about 150 to about 100 mTorr applied for from about 4 to about 48 hours. The resulting shaped material is porous and absorbent and maintains its shape and cohesiveness upon absorption of fluid. The implant can be easily cut with scissors in either the dry or rehydrated state.

Alternatively, a slurry of demineralized elongate bone particles can be injected into a porous tube. The bone particles can be dried and lyophilized in the tube, then removed and cut to length. Examples of suitable porous tubes are dialysis tubing, sausage casings, and rigid metal or plastic tubing perforated with a series of small holes (the holes generally being small enough that a few fibers escape, preferably 0.2 mm or less). It is also possible to use rigid tubing with large holes, and line with another tube that will contain the bone particle slurry such as a flexible dialysis tube. The slurry can be injected into the tube by any suitable means, for example a disposable plastic syringe or a slurry pump. If a thin, flexible tube is used to form the osteoimplant, the osteoimplant can be cut to length (after drying) while inside the tube by cutting through both the tube and the material inside. Alternatively, the dried aggregate elongate bone particles can be removed from the flexible tube (preferably by cutting the tube away) or from a rigid tube (preferably by pushing the material out of the tube) and then cut. Cutting is facilitated by using a cutting jig or guide similar to a cigar cutter or a small double bladed guillotine type of device where the blade spacing equals the desired plug length. Osteoimplants that are dried in a porous tube can have a tougher skin on their outer circumferential surface due to more rapid water loss from the surface than the interior. This can be advantageous in that the osteoimplant will resist insertion and handling forces better. The thickness and toughness of the skin can be influenced by a combination of drying conditions and tubing porosity.

Optionally, the bone particles in the osteoimplant can be crosslinked in accordance employing well-known techniques, e.g., those disclosed in U.S. Pat. No. 6,294,187 the contents which are incorporated by reference herein. These crosslinking procedures result in the formation of chemical bonds between the surface-exposed collagen of mutually contacting surface-demineralized and/or substantially completely demineralized elongate bone particles making up, or contained in, the aggregate of naturally or mechanically entangled elongate bone particles.

Where a mold, e.g., a cylindrical mold, is employed to shape the coherent mass of bone particles into the osteoimplant of this invention, the walls of the mold can be coated with a slurry or paste containing partially and/or fully demineralized bone particles followed by addition of a slurry or paste containing non-demineralized and/or superficially demineralized bone particles (or vice versa). The resulting molded osteoimplant contains at least one region, e.g., an outer surface, composed of partially and/or fully demineralized bone particles and at least one region, e.g., a core, composed of non-demineralized and/or superficially demineralized bone particles. In this manner, the differential in compressive strength, porosity, osteogenicity and other properties between partially and/or fully demineralized bone particles on the one band and non-demineralized and/or superficially demineralized bone particles on the other hand can be exploited. For example, where the osteoimplant is employed in a load-bearing situation, non-demineralized and/or superficially demineralized bone particles can be concentrated in that region of the osteoimplant which will be subjected to an applied load at the implant site.

When the osteoimplant of this invention is fashioned as a plug, the plug can assume a determined or regular form or configuration such as may be desirable for any specific cavity of a commercially available osteoimplant, e.g., spinal cages, or any other relatively well-defined cavity at a surgical site, e.g., extraction sockets, bore holes, etc. Of course, the coherent mass can be machined or shaped by any suitable mechanical shaping means. Computerized modeling can, for example, be employed to provide an intricately-shaped plug which is custom-fitted to a particular cavity of an osteoimplant with great precision. In a preferred embodiment, the plug possesses the configuration of a central cavity of a commercially available spinal cage.

A plug fabricated in accordance with this invention preferably possesses a bone particle content of at least about 5 to about 100 weight percent, preferably at least about 20 weight percent and more preferably at least about 60 weight percent, based on the weight of the entire mass. It will be understood by those skilled in the art that plugs possessing a putty-like consistency will possess lower amounts of bone particles, on a weight-by-weight basis, compared to plugs which are subjected to the drying and lyophilizing and/or compression steps described above.

The foregoing plug can be easily inserted into a cavity of an implant or bone defect site. The plug will often tend to swell somewhat upon contact with irrigation fluids such as those that are commonly used during surgical procedures or upon contact with bodily fluids normally present at the implant site. This swelling has the advantage of providing a tighter fit with the cavity of the osteoimplant or bone defect thus assuring that the plug will remain in place.

The plug can be used for implantation at a surgical site in a variety of ways and for treatment of a variety of bone defects. In certain embodiments, the osteoimplant can be manufactured to contain the plug prior to its packaging and storage. Alternatively, the plug can be provided in a form suitable for placement in an osteoimplant at the time of the implantation of the latter. In yet a further embodiment, the plug described herein is provided in a form suitable for association with one or more osteoimplants or one or more cavities of an osteoimplant after the osteoimplant has been placed at an implant site. In yet a further embodiment, the preformed plug described herein is provided in a form suitable for placement in a relatively well-defined defect site such as, e.g., an extraction socket, bore hole, etc. Of course, any combination of the above-described embodiments may be used depending upon the intended use and/or specific defect site.

In any of the above-described plug embodiments, the plug can be used alone, associated with standard rehydrating solutions such as previously described, associated with autograft tissue such as iliac crest, local bone and/or marrow, blood, plasma or serum obtained at the time of implantation or sometime prior to implantation as well as combinations thereof. In certain embodiments, the plug will be placed at an implant site in the as-packaged condition. In alternative embodiments, the plug can be rehydrated just prior to implantation.

As previously stated, the plug form of the osteoimplant herein can be inserted into the cavity of the implant as is or, if desired, it can be suitably compressed prior to insertion into the implant or defect site. When the plug is compressed just prior to its insertion, any excess liquid or moisture will be displaced from the material as the volume of the plug is temporarily reduced. In this embodiment, the compressed plug, being smaller than its receiving cavity, is easily inserted into such cavity. After relaxation of the applied compressive force, the plug will substantially return to its original volume thus assuring its retention in the cavity.

The foregoing description and embodiments were chosen and described to best explain the principles of the invention and its practical applications, thereby enabling others skilled in the act to best utilize the invention in its various embodiments and with various modifications as are suited to the particular use contemplated. Therefore, the foregoing descriptions of the preferred embodiments of the disclosure herein have been presented for purposes of illustration and description and are not intended to be exhaustive or to limit the invention to the precise forms disclosed. Obviously, many other modifications and variations are possible in light of the above teachings. For example, the plug can be configured to fit a predetermined defect caused at an implant site, e.g., a bore hole of defined diameter and depth. Optionally, the plug can be contacted with fluids such as blood, plasma, serum, bone marrow, etc. obtained from the recipient immediately prior to implantation. Such modifications are also envisioned as being within the scope of the invention herein.

The following examples illustrate the practice of the present invention and in no way limit the scope of the claims appended hereto.

EXAMPLE 1

Process of Making a Species-Specific Osteoimplant with Defined Dimensions.

Species-specific (Rhesus Monkey) long bones were aseptically cleaned. The cortical bone was processed in the bone milling apparatus described in U.S. Pat. No. 5,607,269 to yield 65 grams of elongate bone particles. The elongate bone particles were placed in a reactor and allowed to soak for 5-10 minutes in 0.6N HCl plus 20-2000 ppm nonionic surfactant solution. Following drainage of the HCl/surfactant, 0.6N HCl at 15 ml per gram of total bone was introduced into the reactor along with the elongate bone particles. The reaction proceeded for 40-50 minutes. Following drainage through a sieve, the resulting demineralized elongate bone particles were rinsed three times with sterile, deionized water at 15 ml per gram of total bone, being replaced at 15 minute intervals. Following drainage of the water, the bone particles were covered in alcohol and allowed to soak for at least 30 minutes. The alcohol was then drained and the bone particles were rinsed with sterile deionized water. The bone particles were then contacted with a mixture of 4.5 ml glycerol per gram of dry bone particles and 10.5 ml sterile, deionized water per gram of dry bone particles for at least 60 minutes. Excess liquid was drained and the resulting liquid composition containing approximately 11 (w/v) demineralized elongate bone particles was transferred to a 11 cm×11 cm mold containing a lid having a plurality of protruding indentations such as those depicted in FIG. 4. The dimensions of the protrusions were specific for the size of the osteoimplant required for the Rhesus monkey. The lid was gently placed on the mold such that the indentations became immersed into the liquid composition to exert as little pressure on the composition as possible. The mold was then placed in an oven at 46° C. for 4 hours. The composition was then frozen overnight at −70° C. and then lyophilized for 48 hours. Following lyophilization, the mold was disassembled and the formed composition was cut into individual pieces that contained troughs corresponding to the dimensions of the lid protrusions. The resulting pieces had dimensions of 4.5 cm in length, 2.5 cm in width and about 8 mm in height with trough dimensions of 3.5 cm in length, 1 cm in width and 4 mm of depth.

The resulting composition was cohesive, flexible, and sponge-like with an obvious continuous three-dimensional structure possessing visible open pores. The implant had a defined shape including the indentations made by the lid protrusions, did not require rehydration before use, and was more rapidly hydratable in comparison to Grafton®Flex. The material retained its shape once wetted with fluids and freezing was not required for storage.

The density of bone is based on calculation of the defined mold volume used and the amount of demineralized bone particles used to fill the volume of the mold. In making the composition described in this example, 12 g demineralized fibers occupied a volume of 105 cm$^3$. Therefore, the density was approximately 0.114 g of bone/cm$^3$. These calculations are approximate as there can be a range in weights (about 10-20 g) and a range in volumes of about 100-120 cm$^3$ (which can be defined by the dimensions of the mold used).

EXAMPLE 2

Evidence of Osteoinduction by Grafton DBM in Non-Human Primate Spine Fusion.

While autogenous iliac crest bone graft remains the "gold standard", much work continues to identify viable bone graft extenders, enhancers, and substitutes. While several demineralized bone matrix formulations have been shown to be variably osteoinductive in rodent ectopic bone assays, few have demonstrated efficacy in higher species and more challenging applications such as posterolateral spine fusion. To date, none have been tested in a non-human primate posterolateral spine fusion model which has been previously determined to be extremely challenging with less than 40% of animals achieving successful fusion with autogenous iliac crest bone graft. The purpose of this example was to test the osteoimplant described in Example 1 for evidence of osteoinduction and its use as an extender/enhancer for autogenous bone graft in a non-human primate.

Four skeletally mature rhesus macaques underwent single level lumbar posterolateral arthrodesis through a Wiltse muscle-splitting approach under general anesthesia. The transverse processes were decorticated with an electric burr. Autogenous iliac crest bone graft was harvested bilaterally through separate fascial incisions. In these four animals, rhesus-specific osteoimplant material (described in Example 1) was implanted with the usual autograft (4 g) on one side of the spine and one half the usual autograft (2 g) on the opposite side. Radiographs were taken at intervals until euthanasia at 24 weeks. The lumbar spines were excised and palpated manually to determine fusion status as fused or not fused and then underwent CT scanning to visualize the amount of bone formation. Radiographs and CT scans were evaluated blindly and assessed semi-quantitatively for the area of the fusion mass (3=good, 2=fair, 1=poor) and the amount of bridging between the transverse processes on each side (0=<25%, 1=25%, 2=50%, 3=75%, 4=100%). Points were added for each site in each animal. Three of four monkeys receiving the osteoimplant plus autograft were graded as fused. Six of eight sites in the were rated as "good" for area of fusion mass on CT (computer tomography) scans. Six of eight sites had at least 50% bridging. The quality and amount of bone was better in the osteoimplant group and best with the 4 g of autograft. Although the assessment of bone formation was semi-quantitative, given the spectrum of fusions previously obtained in this model with autograft alone, these data support evidence of osteoinduction of the osteoimplant in a challenging model. These data support the role of this osteoimplant as an osteoinductive graft extender and graft enhancer in rhesus posterolateral spine fusion.

EXAMPLE 3

Implantation of Osteoimplant in a Human Patient to Promote Spinal Fusion.

Human-specific osteoimplant was made in the same manner described in Example 1. However, the mold dimensions and final dimensions of the osteoimplant were altered to adjust to the approximate size required for human posterolateral spinal fusion procedure (known by those skilled in the art). The dimensions of the osteoimplant pieces were approximately 5.0 cm in length, 2.5 cm in width and approximately 1 cm in height with trough dimensions 4 cm in length, 1.5 cm in width and depth approximately 0.7 cm. The trough design specifically allowed for the surgeon to fill the center of the osteoimplant with autograft or allograft or both. Autograft is usually obtained from local bone at the site of the procedure, or marrow, or iliac crest or a combination. The fluids rapidly dispersed within the osteoimplant hydrating the osteoimplant. The osteoimplant is placed either trough down facing the decorticated transverse processes or trough facing away from the decorticated transverse processes to allow blood to be absorbed by the sponge-like nature of the osteoimplant. The osteoimplant remains as a three-dimensional cohesive structure retaining the autograft or allograft or both at the implant site. The surgery then follows usual closure procedure known to those skilled in the art.

EXAMPLE 4

Evaluation of the Osteoinductive Potential of Example 1.

The osteoinductive potential of Example 3 (human-specific osteoimplant) for posterolateral fusion (PLF) was evaluated using the standard heterotopic osteoinductive implant model (see, Edwards J T, Diegmann M H, Scarborough N L, Osteoinduction of human demineralized bone: Characterization in an animal model, Clin Orthop Rel Res 357:219228 (1998) which is a modification of Urist MR, Bone formation by autoinduction, Science, 150:893-899 (1965)). Implants are placed in the hind limb, intramuscular sites of athymic rats and evaluated histologically after 28 days.

Animal Model

The study was conducted in the athymic (nude) rat to minimize the potential for a cross species incompatibility response to xenograft tissue implants. The hind-limb intramuscular site is ideal for the initial determination of heterotopic bone induction properties of implant materials, as bone is not present in this area.

Implant Placement

The study utilized a singular intramuscular (IM) implantation site in each hind limb of the animals. Different specimen types were placed in the sites in a randomized fashion, such that the same animal did not have the same treatment in both hind limbs. To provide a common positive control over all animals, a single 40 mg sample of rat DBM powder was placed intramuscularly over the left pectoralis (LP) muscle on the left side of each rat. Animals were allowed normal activities following surgical procedures. Four samples of each material were used for analysis.

Procedure

Briefly, rats were anesthetized with a mixture of ketamine (250 mg), xylazine (11 mg), and physiological saline (10 ml). The dosage is 3.6 ml/kg body weight administered intraperitoneally. Aseptic surgical procedures were carried out in a laminar airflow hood. A 1 cm skin incision was made on each upper hind limb using a lateral approach and the skin was separated from the muscle by blunt dissection. A superficial incision aligned with the muscle fiber plane was made to allow for insertion of the tips of the scissors. Blunt dissection of the muscle to create a pocket and positioning of the rat DBM powder or devitalized fibers was made using a blunt syringe. In each case, the skin was closed with metal clips.

Rats were euthanized with $CO_2$ following 28-day implantation time. Implant materials were located by palpitation, retrieved by blunt dissection and cleaned of the surrounding tissue by careful trimming. An observer blinded to implant type performed a macroscopic evaluation of the implant material. Color, vascularity, hardness and integrity were scored according to the scheme outlined in Table I; the highest score for the most robust response would be 1, while a specimen showing little or no osteoinductive potential would score 0. Experience with this model has shown a high correlation between visual observations and histological observations of DBM implant performance.

Histology

Retrieved materials were fixed in neutral buffered formalin, dehydrated in a series of graded ethanol solutions, embedded in JB-4 (glycol methacrylate, Polysciences, Inc., Warrington, Pa.) and sectioned. Toluidine blue was used for staining and each material was evaluated using a light microscope at magnifications up to 200×.

A numerical score of 0, 1, 2, 3, or 4 was given to grade the extent of new bone formation for each explant when examined under the light microscope. Assignment of scores was according to the descriptions given in Table II below. Histological sections for each explant were scored independently by two individuals blinded to treatment groups.

Following histological analysis, average scores were calculated for each material type or sample group. Based on previous experience with this animal model, each group was assigned an assessment of osteoinductive potential based on the average histological scores. Sample groups scoring 0 show "no osteoinductive response"; groups scoring up to 2 show a "slight osteoinductive response" and groups scoring 3 or above show a "robust osteoinductive response".

TABLE I

| Macroscopic Observation Scoring Guidelines | | | |
|---|---|---|---|
| Color | White (W) | Gray(G) | Red (R) |
| Vascularity | None (N) | Some (S) | Robust (R) |
| Hardness | Mushy (M) | Firm (F) | Hard (H) |
| Integrity | Diffuse (D) | Flat (F) | Nodule (N) |
| Score | 0 | 0.5 | 1 |

TABLE II

| Scoring of Histological Sections | |
|---|---|
| Score | New Bone Formation |
| 0 | No new bone |
| 1 | Few areas of new bone formation |
| 2 | Numerous areas of new bone formation |
| 3 | Greater than 50% of nodule involved in new bone formation |
| 4 | Greater than 75% of nodule involved in new bone formation |

Results

Histology showed evidence of robust cartilage, bone and marrow formation in the samples. Scores for the individual samples were averaged and the mean±SD of the osteoinductive score for 13 individual samples derived from Example 3 was 3.3±0.7. Historically, demineralized bone powder produces a comparable osteoinductive score of 3.6±0.8 while guanidine hydrochloride extracted samples routinely display lack of inductivity. The foregoing results demonstrate that the osteoimplant of the invention possesses excellent osteoinductivity with the additional advantage of being a cohesive three-dimensional, lower density, porous matrix.

EXAMPLE 5

Figure 1A:
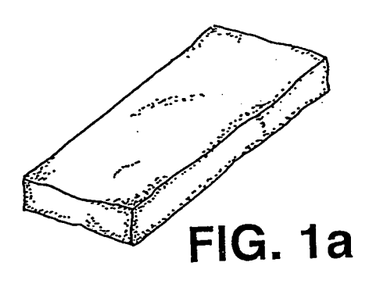
FIG. 1 is a non-limiting representation of particular sizes and shapes of osteoimplants prepared and used as described herein.
Figure 1B:
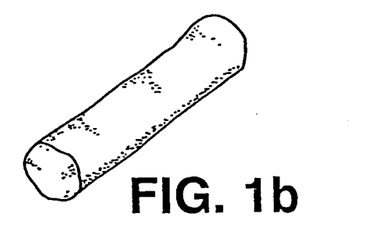
Figure 1C:
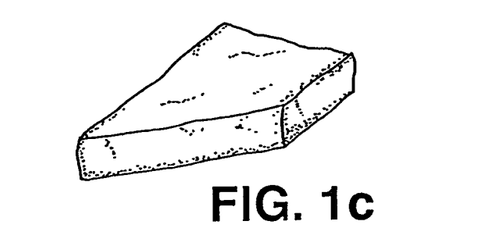
Figure 1D:
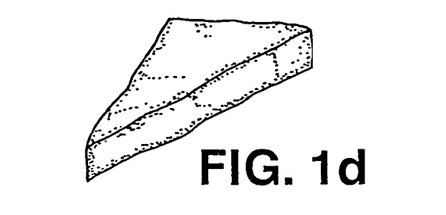
Figure 1E:
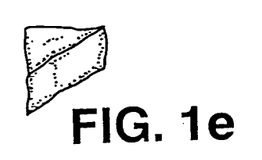
Figure 1F:
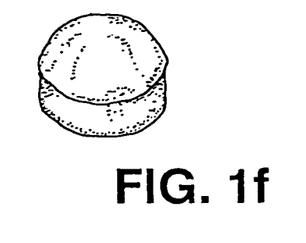
Figure 1G:
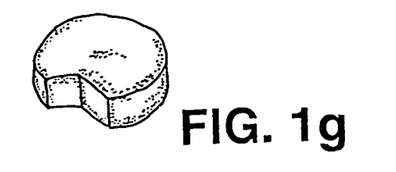
Figure 1H:
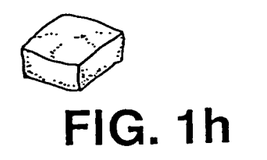
Figure 1I:
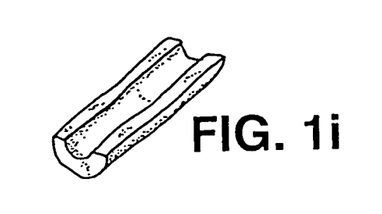
Figures 2, 2A:
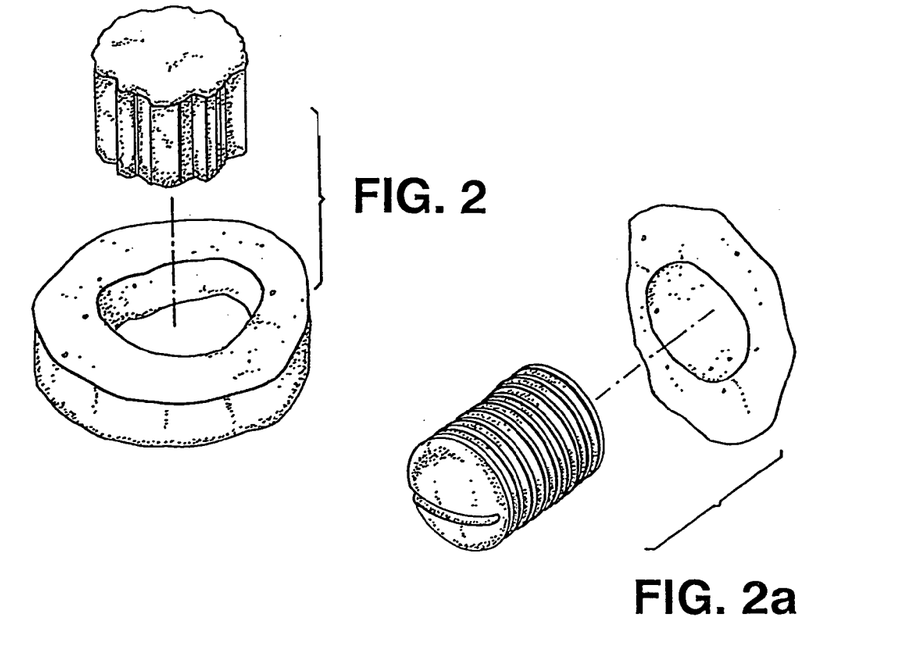
FIG. 2 is a non-limiting representation of an intervertebral implant, specifically, a diaphyseal ring, containing a plug in accordance with the invention.
Figure 3:
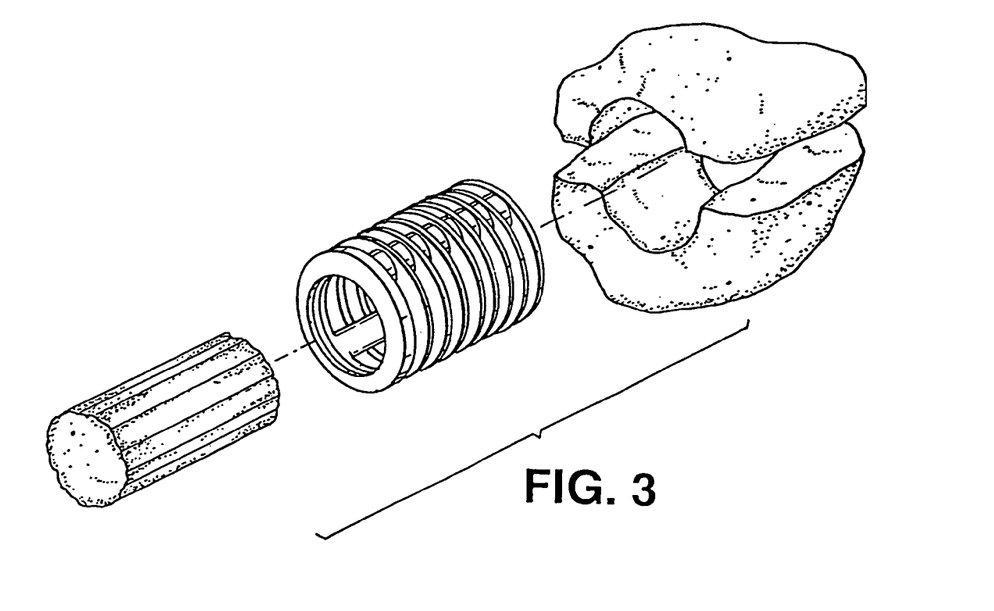
FIG. 3 is a non-limiting representation of a fusion cage whose void space is filled with a plug in accordance with the invention.

This example illustrates the preparation of a plug in accordance with the invention which is intended for insertion in the cavity of an implant as shown in FIGS. 2, 2a and 3, or in the cavity of a bone defect site.

Mineralized milled and sieved fibers of cortical bone were fully demineralized with a 30 ml volume of 0.6M HCl/0.025% Triton X-100 per gram of bone at room temperature. The acid was decanted and the remaining fibers were washed with deionized water to remove the remaining acid. The demineralized elongate fibers were soaked in a 70% ethanol and deionized water solution for at least 30 minutes. The elongate demineralized fibers were washed with deionized water to remove the ethanol solution. The wet elongate demineralized fibers were added to a glycerol-deionized water solution and mixed well. The fibers and the glycerol-deionized water solution was allowed to sit for at least one hour. The elongate demineralized fibers were lightly packed in a cylindrical vessel to form a mold with a desired configuration which was capped to prevent loss of moisture. The capped vessel was heated in an oven at 46 degrees Celsius for a period of from two to six hours. The capped vessel was then placed in a freezer for from 6 to 24 hours at −70 degrees Celsius. The vessel was then removed from the freezer and the cap was removed. The uncapped vessel was then lyophilized for 48 hours. The lyophilized plug was then removed from the container.

What is claimed is:

1. An osteoimplant which comprises a coherent aggregate of elongate bone particles selected from the group consisting of substantially fully demineralized elongate bone particles, partially demineralized elongate bone particles, superficially demineralized elongate bone particles, and mixtures thereof, wherein mutually contacting elongate bone particles are mechanically entangled with each other, the coherent aggregate of elongate bone particles being shaped in a mold to predetermined dimensions in the substantial absence of pressure or mechanical shaping forming an open pore, sponge-like structure, wherein the open pore, sponge-like structure enables the osteoimplant to absorb fluids while generally retaining the predetermined shape.

2. The osteoimplant of claim 1 wherein the elongate bone particles represent at least about 50 weight percent of the aggregate.

3. The osteoimplant of claim 1 wherein the elongate bone particles represent at least about 60 weight percent of the aggregate.

4. The osteoimplant of claim 1 wherein the elongate bone particles represent at least about 90 weight percent of the aggregate.

5. The osteoimplant of claim 1 wherein the aggregate further comprises non-elongate bone particles.

6. The osteoimplant of claim 5 wherein at least some of the non-elongate bone particles are substantially fully mineralized, substantially fully demineralized, partially demineralized or superficially demineralized.

7. The osteoimplant of claim 1 wherein the elongate bone particles are obtained from cortical, cancellous, corticocancellous allogenic, xenogenic or transgenic bone tissue.

8. The osteoimplant of claim 1 wherein the elongate bone particles possess the capability to facilitate or accelerate new bone growth by at least one of osteogenesis, osteoconduction and osteoinduction.

9. The osteoimplant of claim 1 wherein the median length of the elongate bone particles is from about 2 to about 200 mm, the median width of the elongate bone particles is from about 0.05 to about 50 mm and the ratio of median length to median width is from about 10:1 to about 2000:1.

10. The osteoimplant of claim 1 wherein the median length of the elongate bone particles is from about 1 to about 100 mm, the median width of the elongate particles is from about 0.1 to about 20 mm and the ratio of median length to median width is from about 20:1 to about 600:1.

11. The osteoimplant of claim 1 wherein at least some of the elongate bone particles are substantially fully demineralized.

12. The osteoimplant of claim 1 wherein elongate bone particles are admixed with one or more of the group consisting of binders/fillers, plasticizers, biostatic/biocidal agents, bioactive substances, surface active agents prior to, during and/or after forming the aggregate into the osteoimplant.

13. The osteoimplant of claim 12 wherein the binder/filler is selected from the group consisting of cyanoacrylates, epoxy-based compounds, dental resin sealants, dental resin cements, calcium phosphate and calcium sulfate self-setting cements, glass ionomer cements, polymethyl methacrylate, gelatin-resorcinol-formaldehyde glues, protein and collagen-based glues, acrylic resins, cellulosics, bioabsorbable polymers such as polyglycolide, polylactide, glycolide-lactide copolymers, polycaprolactone, polyanhydrides, polycarbonates, polyorthoesters, polyamino acids, polyarylates, polycyanoacrylates, polyhydroxybutyrate, polyhydroxyvalyrate, polyphosphazenes, polyvinylpyrrolidone, polyarylates, tyrosine-based polycarbonates and polyarylates, carbohydrate polymers, polyiminocarbonates, polypropylene fumarates, polyanhydride esters, polytetrafluroethylene, hexacryl, Hyaluronic acid, fibrin, fibrin-collagen, polyethylene glycol glues, mucopolysaccharides and mussel adhesive proteins, fatty acids and fatty acid derivatives.

14. The osteoimplant of claim 12 wherein the binder/filler is selected from the group consisting of bone powder, demineralized bone powder, porous calcium phosphate ceramics, hydroxyapatite, tricalcium phosphate, Bioglass.RTM. and other calcium phosphate materials, calcium sulfate or calcium carbonate particles.

15. The osteoimplant of claim 12 wherein the plasticizer is selected from the group liquid polyhydroxy compound.

16. The osteoimplant of claim 15 wherein the liquid polyhydroxy compound is glycerol.

17. The osteoimplant of claim 12 wherein the biostatic/biocidal agent is selected from the group consisting of antibiotics, povidone, sugars and mucopolysaccharides.

18. The osteoimplant of claim 12 wherein the surface-active agent is selected from the group consisting of biocompatible nonionic, cationic, anionic and amphoteric surfactant.

19. The osteoimplant of claim 12 wherein the bioactive substance is selected from the group consisting of trophic factors, analgesics, anti-cancer agents, vaccines, adjuvants, antibodies, neuroleptics, cells or cellular components, collagen, insoluble collagen derivatives, and soluble solids and/or liquids dissolved therein, antiviricides; antimicrobials and/or antibiotics; biocidal/biostatic sugars; amino acids, peptides, vitamins, inorganic elements, co-factors for protein synthesis; hormones; endocrine tissue or tissue fragments, synthesizers; enzymes, polymer cell scaffolds with parenchymal cells, angiogenic drugs and polymeric carriers containing such drugs; collagen lattices; antigenic agents; cytoskeletal agents; cartilage fragments, modified living cells, natural extracts, genetically engineered living cells, DNA delivered by plasmid or viral vectors, tissue transplants, demineralized bone powder, autogenous tissues, blood, serum, soft tissue, bone marrow, bioadhesives; non-collagenous proteins, osteopontin, osteonectin, bone sialo protein, laminin, fibrinogen, vitronectin, thrombospondin, proteoglycans, decorin, beta glycan, biglycan, aggrecan, versican, tenascin, matrix gla protein, hyaluronan, amino acids, amino acid residues, peptides, bone morphogenic proteins (BMPs); osteoinductive factor (OIF); fibronectin (FN); endothelial cell growth factor (ECGF); cementum attachment extracts (CAE); ketanserin; human growth hormone (HGH); animal growth hormones; epidermal growth factor (EGF); interleukin-1 (L-1); human alpha thrombin; transforming growth factor (TGF-beta); insulin-like growth factor (IGF-1) (IGF-2); platelet derived growth factors (PDGF); fibroblast growth factors (FGF, aFGF, bFGF, etc.); periodontal ligament chemotactic factor (PDLGF); somatotropin; bone digestors; antitumor agents; immuno-suppressants; fatty acids; permeation enhancers, fatty acid esters, laureate, myristate and stearate monoesters of polyethylene glycol, enamine derivatives, alpha-keto-aldehydes, and nucleic acids; inorganic elements, inorganic compounds, cofactors for protein synthesis, hormones, soluble and insoluble components of the immune system; soluble and insoluble receptors; soluble, insoluble and cell surface bound ligands; chemokines, bioactive compounds that are endocytosed; endocrine tissue or tissue fragments, growth factor binding proteins, insulin-like growth factor binding protein (IGFBP-2) (IGFBP-4) (IGFBP-5) (IGFBP-6); angiogenic agents, bone promoters, cytokines, interleukins, genetic material, genes encoding bone promoting actions, cells containing genes encoding bone promoting action; growth hormones; bone digestors; antiumor agents; cellular attractants and attachment agents; immunosuppressants; bone resorption inhibitors and stimulators; angiogenic and mitogenic factors; bioactive factors that inhibit and stimulate secondary messenger molecules; cell adhesion molecules, cell-matrix and cell-cell adhesion molecules; secondary messengers, monoclonal antibodies specific to cell surface determinants on mesenchymal stem cells, clotting factors; externally expanded autograft or xenograft cells, nucleic acids and any combination thereof.

20. The osteoimplant of claim 1 wherein the elongate bone particles are in the lyophilized state.

21. The osteoimplant of claim 1 wherein the elongate bone particles are cross-linked.

22. The osteoimplant of claim 1 possessing regions one of which comprises demineralized elongate bone particles and another of which comprises nondemineralized elongate bone particles.

23. The osteoimplant of claim 22 wherein the region of demineralized elongate bone particles defines at least a portion of the exterior surface of the osteoimplant and the region of mineralized elongate bone particles defines at least a portion of core of the osteoimplant.

24. The osteoimplant of claim 1 possessing a bulk density of not greater than about 0.3 g/cm.

25. The osteoimplant of claim 1 in the shape of a sheet, plate, disk, cone, pin, screw, tube, tooth, tooth root, plug, bone or portion of bone, wedge or portion of wedge, cylinder or threaded cylinder.

26. The osteoimplant of claim 1 possessing at least one recess therein.

27. The osteoimplant of claim 1 wherein the elongate bone particles possess a ratio of median length to median width of from about 10:1 to about 2000:1.

28. The osteoimplant of claim 1 wherein the elongate bone particles possess a ratio of median length to median width of from about 20:1 to about 600:1.

29. The osteoimplant of claim 1 wherein the osteoimplant is configured for use in posterolateral procedures.

30. An implant for bone repair possessing at least one cavity containing the osteoimplant of claim 1.

31. The implant of claim 30 which is an intervertebral implant.

32. The implant of claim 30 which is a fusion cage.

* * * * *